United States Patent [19]

von der Saal et al.

[11] Patent Number: 4,882,342

[45] Date of Patent: Nov. 21, 1989

[54] 5-ALKYLBENZIMIDAZOLES, METHOD OF USE AND PHARMACEUTICAL COMPOSITIONS

[75] Inventors: Wolfgang von der Saal, Weinheim; Jens-Peter Hölck, Mannheim; Alfred Mertens, Schriesheim; Bernd Müller-Beckmann, Grünstadt; Lothar Kling, Mannheim, all of Fed. Rep. of Germany

[73] Assignee: Boehringer Mannheim GmbH, Mannheim, Fed. Rep. of Germany

[21] Appl. No.: 106,413

[22] Filed: Oct. 6, 1987

[30] Foreign Application Priority Data

Oct. 7, 1986 [DE] Fed. Rep. of Germany ....... 3634066

[51] Int. Cl.⁴ .................. C07D 401/04; C07D 401/12; A61K 31/415
[52] U.S. Cl. ...................................... 514/338; 514/253; 514/254; 514/255; 514/397; 514/365; 514/372; 514/374; 514/378; 514/383; 514/381; 514/362; 514/363; 514/269; 514/241; 514/317; 546/271; 546/199; 546/144; 546/148; 546/153; 546/167; 548/221; 548/222; 548/241; 548/159; 548/209; 548/212; 548/334; 548/325; 548/329; 548/327; 548/181; 548/214; 548/206; 548/233; 548/215; 548/245; 548/246; 548/255; 548/266; 548/252; 548/254; 548/251; 548/127; 548/128; 548/133; 548/131; 548/134; 548/135; 548/137; 548/136; 548/143; 548/328; 544/405; 544/324; 544/322; 544/333; 544/238; 544/148; 544/212; 544/180; 544/179; 544/370; 544/235; 544/237
[58] Field of Search ........................ 546/271; 514/338

[56] References Cited

U.S. PATENT DOCUMENTS

| | | | |
|---|---|---|---|
| 4,188,486 | 2/1980 | Tsukamoto et al. | 546/271 |
| 4,532,248 | 7/1985 | Franckowiak et al. | 514/302 |
| 4,563,455 | 1/1986 | Ueda et al. | 546/271 |
| 4,714,764 | 12/1987 | Sato et al. | 546/271 |

Primary Examiner—Jane T. Fan
Attorney, Agent, or Firm—Felfe & Lynch

[57] ABSTRACT

The present invention concerns new 5-alkylbenzimidazoles of the formula:

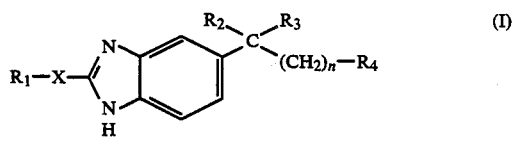

(I)

wherein $R_1$ is a phenyl ring of the formula:

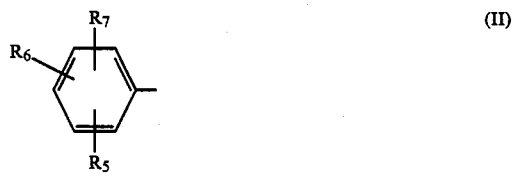

(II)

or $R_1$ is naphthyl, heterocycle or a bicyclic heterocycle and $R_1$-$R_7$ are described in claim 1.

These compounds are useful for prophylaxis or treatment of heart and circulatory disease especially to increase contractility of the heart, lower blood pressure and/or influence the thrombocyte function and improve the microcirculation.

17 Claims, No Drawings

5-ALKYLBENZIMIDAZOLES, METHOD OF USE AND PHARMACEUTICAL COMPOSITIONS

The present invention is concerned with new 5-alkylbenzimidazoles, processes for the preparation thereof and pharmaceutical compositions containing them.

The new 5-alkylbenzimidazoles according to the present invention are compounds of the general formula:

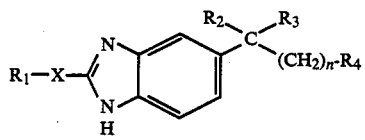

wherein $R_1$ is a phenyl ring of the general formula:

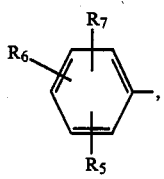

wherein $R_5$, $R_6$ and $R_7$, which can be the same or different, are hydrogen atoms, alkanesulphonyloxy, trifluoromethanesulphonyloxy, alkanesulphonylamino, trifluoromethanesulphonylamino, N-alkyl-alkanesulfphonylamino, N-alkyltrifluoromethanesulphonylamino, alkylsulphenylmethyl, alkylsulphinylmethyl or alkylsulphonylmethyl radicals, carbonyl groups substituted by a hydroxyl, alkoxy, amino, alkylamino or dialkylamino group, sulphonyl groups substituted by an amino, alkylamino, dialkylamino or cyclic imino group, whereby a methylene group can be replaced by a sulphur or oxygen atom, alkylcarbonylamino, aminocarbonylamino or alkylaminocarbonylamino radicals, alkylthio, alkylsulphinyl or alkylsulphonyl radicals, nitro groups, halogen atoms, amino or hydroxyl groups, alkyl, alkoxy, alkenyloxy, alkynyloxy, cyanoalkyloxy, carboxyalkyloxy, alkoxycarbonylalkyloxy, dialkylamino, 1-imidazolyl or trifluoromethyl radicals or cyano groups, or is a naphthyl radical or a heterocyclic five-membered ring with 1-4 heteroatoms or a heterocyclic six-membered ring with 1-5 heteroatoms, the heteroatoms being the same or different and being oxygen, sulphur or nitrogen which, if desired, can carry an oxygen atom on one or more nitrogen atoms and the five- and six-membered rings are optionally substituted by one or more alkyl, alkoxy, alkylthio, hydroxyl, nitro, amino, halogen or cyano groups or optionally condensed with a phenyl ring to form a bicycle, or, for the case in which X represents a valency bond, $R_1$, besides the above-mentioned groups, can also signify a hydrogen atom, an alkyl, cycloalkyl, alkenyl, cycloalkenyl, alkynyl, haloalkyl, alkoxyalkyl, carboxyalkyl, alkoxycarbonylalkyl, aminoalkyl, hydroxyl, mercapto, amino, alkylthio, alkylcarbonylamino, formylamino, alkylsulphonylamino, formylaminoalkyl, alkoxycarbonylaminoalkyl or alkylsulphonylaminoalkyl radical, $R_2$ and $R_3$, which can be the same or different, are hydrogen atoms or alkyl radicals or $R_2$ and $R_3$, together with the carbon atom to which they are attached, represent a carbocyclic ring, $R_4$ is a cyano, aminocarbonyl, alkylaminocarbonyl, dialkylaminocarbonyl, hydroazinocarbonyl or amino group, the hydrazinocarbonyl or the amino group being, if desired, substituted by a formyl, alkylcarbonyl, trifluoromethylcarbonyl, alkylsulphonyl, trifluoromethylsulphonyl, phenylsulphonyl, alkylaminocarbonyl or dialkylaminocarbonyl radical, X is a valency bond, an alkylene, vinylene or imino group —NH— or a carbonylamino group —CONH— and n is 0 or 1 to 5, the tautomers thereof and the physiologically acceptable salts thereof with inorganic and organic acids.

Since the compounds of general formula I possess an asymmetric carbon atom, the present invention also includes the optically—active forms and racemic mixtures of these compounds.

The new compounds of the present invention display valuable pharmacological properties and, in particular, they bring about on desquamated heart muscle fibres an increase of the sensibility to calcium ions and can thus be used as agents for increasing the contractility of the heart. Furthermore, they lower the blood pressure and/or influence the thrombocyte function and improve the microcirculation.

When $R_1$ is a phenyl ring of general formula (II), then the alkyl moiety of the substituents mentioned in the case of $R_5$, $R_6$ and $R_7$ can contain up to 5 and preferably up to 4 carbon atoms. Preferred substituents include, for example, the methanesulphonyloxy, ethanesulphonyloxy, n-propanesulphonyloxy, isopropanesulphonyloxy, trifluoromethanesulphonyloxy, methylsulphenylmethyl, ethylsulphenylmethyl, n-propylsulphenylmethyl, methylsulphinylmethyl, ethylsulphinylmethyl, n-propylsulphinylmethyl, methylsulphonylmethyl, ethylsulphonylmethyl, n-propylsulphonylmethyl, methanesulphonylamino, ethanesulphonylamino, n-propanesulphonylamino, trifluoromethanesulphonylamino, N-methyl-methanesulphonylamino, N-ethyl-methanesulphonylamino, N-methylethanesulphonylamino, N-ethyl-ethanesulphonylamino, N-isopropyl-ethanesulphonylamino, N-methyl-n-propanesulphonylamino, N-n-propyl-n-propanesulphonylamino, N-methyl-trifluoromethanesulphonylamino, N-ethyltrifluoromethanesulphonylamino, N-isopropyl-trifluoromethanesulphonylamino, methoxycarbonyl, ethoxycarbonyl, propoxycarbonyl, isopropoxycarbonyl, methylaminocarbonyl, ethylaminocarbonyl, dimethylaminocarbonyl, di-n-propylaminocarbonyl, N-methyl-ethylaminocarbonyl, trifluoromethyl, methylaminosulphonyl, ethylaminosulphonyl, n-propylaminosulphonyl, n-butylaminosulphonyl, n-pentylaminosulphonyl, dimethylaminosulphonyl, diethylaminosulphonyl, di-n-propylaminosulphonyl, N-methyl-isopropylaminosulphonyl, acetylamino, propionylamino, methylcarbonylamino, ethylaminocarbonylamino, propylaminocarbonylamino, methyl, ethyl, propyl, methoxy, ethoxy, propyloxy, allyloxy, but-2-enyloxy, but-3-enyloxy, pent-2-enyloxy, propargyloxy, but-2-ynyloxy, but-3-ynyloxy, cyanomethyloxy, cyanoethyloxy, methoxycarbonylmethyloxy, methoxycarbonylethyloxy, methylthio, ethylthio, methylsulphinyl, ethylsulphinyl, methylsulphonyl and ethylsulphonyl radicals.

In the case of sulphonyl groups which can be substituted by cyclic imino groups, there are preferred the morpholino-, pyrrolidino-, piperidino- and hexamethyleneiminosulphonyl radicals.

In particular, $R_5$ is preferably a hydrogen atom or an alkylsulphonyloxy, trifluoromethylsulphonyloxy, alkylsulphenylmethyl, alkylsulphinylmethyl, alkylsulphonylmethyl, alkylsulphonylamino, N-alkyl-alkylsulphonylamino, trifluoromethylsulphonylamino or N-alkyltrifluoromethylsulphonylamino radical, a carbonyl group substituted by a hydroxyl, alkoxy, amino, alkylamino or dialkylamino radical or a sulphonyl group substituted by an amino, dialkylamino or morpholino radical, the above-mentioned alkyl moieties preferably containing 1 or 2 carbon atoms, a nitro or cyano group or an alkylaminosulphonyl radical containing up to 4 carbon atoms, an alkylcarbonylamino, aminocarbonylamino, N-alkylaminocarbonylamino, alkylthio, alkylsulphinyl or alkylsulphonyl radical, each of the above-mentioned alkyl moieties preferably containing 1 to 2 carbon atoms, halogen, amino, hydroxyl, dialkylamino, alkyl, alkoxy, alkenyloxy or alkynyloxy radicals preferably containing up to 3 carbon atoms, a cyanomethyloxy or methoxycarbonylmethyloxy radical, a trifluoromethyl radical or a 1-imidazolyl radical, $R_6$ is preferably a hydrogen atom or an alkyl radical containing up to 3 carbon atoms, an alkoxy or dialkylamino radical containing 1 or 2 carbon atoms in each alkyl moiety or a halogen atom and $R_7$ is preferably a hydrogen atom or methoxy radical.

The phenyl moiety can contain up to 3 of the said substituents.

Preferred monosubstituted phenyl compounds are the hydroxy-, $C_1$–$C_3$-alkyl-, $C_1$–$C_3$-alkoxy-, allyloxy-, propargyloxy-, cyanomethyloxy-, methoxycarbonylmethyloxy-, halogen-, nitro-, cyano-, aminocarbonyl-, methoxycarbonyl-, amino-, $C_1$–$C_3$-dialkylamino-, $C_1$–$C_3$-alkylthio-, $C_1$–$C_3$-alkylsulphinyl-, $C_1$–$C_3$-alkylsulphonyl-, $C_1$–$C_3$-alkylsulphonyloxy- and 1-imidazolyl-phenyls, the substituent being in the 2-, 3- or 4-position.

Preferred disubstituted phenyls contain, as substituents, alkanesulphonyloxy, trifluoromethylsulphonyloxy, alkylsulphenylmethyl, alkylsulphinylmethyl, alkylsulphonylmethyl, alkylsulphonylamino, N-alkyl-alkylsulphonylamino, trifluoromethylsulphonylamino or N-alkyl-trifluoromethylsulphonylamino radicals, carbonyl groups substituted by a hydroxyl, alkoxy, amino, alkylamino or dialkylamino radical or sulphonyl groups substituted by an amino, dialkylamino or morpholino radical, alkylaminosulphonyl, alkylcarbonylamino, aminocarbonylamino or N-alkyl-aminocarbonylamino radicals, hydroxyl, alkyl, alkoxy, allyloxy, propargyloxy, cyanomethyloxy, methoxycarbonylmethyloxy, cyano, halogen, nitro, amino, dialkylamino, alkylthio, alkylsulphinyl, alkylsulphonyl or 1-imidazolyl radicals, the two substituents thereby being the same or different and being in the 2,3-, 2,4-, 2,5-, 2,6-, 2,4- or 3,5-position but preferably in the 2,4-, 2,5- and 3,4-position and the above-mentioned alkyl radicals, alone or in combination with other radicals, can contain up to 3 carbon atoms.

A preferred trisubstituted phenyl radical is the 3,4,5-trimethoxyphenyl radical.

When $R_1$ is a heterocyclic five-membered ring with 1–4 heteroatoms or a heterocyclic six-membered ring with 1–5 heteroatoms, the heteroatoms of the above-mentioned five- and six-membered rings being the same or different and signifying nitrogen, oxygen or sulphur and optionally having an oxygen on one or more nitrogen atoms, then they are preferably pyrrole, furan, thiophene, pyrazole, imidazole, thiazole, isothiazole, oxazole, isoxazole, triazole, tetrazole, thiadiazole, oxadiazole, pyrazine, N,N'-dioxypyrazine, pyrimidine, N,N'-dioxypyrimidine, pyridazine, oxazine, thiazine, triazine, tetrazine, pyridyl, N-oxypyridyl, piperidine, piperazine, morpholine or thiomorpholine radicals.

Alkyl, alkoxy and alkylthio substituents in the heterocyclic five- and six-membered rings can contain up to 6 and preferably up to 4 carbon atoms, the methyl, ethyl, methoxy, ethoxy, methylthio and ethylthio radicals being preferred. Halogen is to be understood to be fluorine, chlorine or bromine, chlorine being preferred.

If the heterocyclic five- and six-membered rings are condensed with a phenyl ring, then there are preferred the indole, indazole, benzimidazole, quinoline, isoquinoline, cinnoline, phthalazine, quinazoline, quinoxaline, benzofuran, benzothiophene, benzoxazole, benzisoxazole, benzothiazole and benzisothiazole radicals, as well as the naphthyl radical.

If X is a valency bond and $R_1$ is an alkyl, alkenyl or alkynyl radical, then there is to be understood thereunder straight and branched chains containing up to 8 carbon atoms, preferably a methyl, ethyl, propyl, butyl, pentyl, hexyl, vinyl, propenyl or propynyl radical. If X is a valency bond and $R_1$ is a cycloalkyl or cycloalkenyl radical, then there are to be understood thereunder rings containing three to seven members. Preferred in this sense is the cyclopropyl, cyclobutyl, cyclopentyl, cyclohexyl, cyclopentenyl and cyclohexenyl radical. If X is a valency bond and $R_1$ is an alkoxyalkyl, carboxyalkyl, alkoxycarbonylalkyl, hydroxyalkyl, aminoalkyl, alkylamino or alkylaminocarbonyl radical, then the alkyl and alkoxy moieties can contain up to 6 carbon atoms.

Preferred in this sense is the ethoxymethyl, methoxyethyl, ethoxyethyl, carboxymethyl, carboxypropyl, carboxybutyl, methoxycarbonylmethyl, methoxycarbonylethyl, methoxycarbonylpropyl, ethoxycarbonylmethyl, ethoxycarbonylethyl, ethoxycarbonylpropyl, propoxycarbonyl ethyl, aminomethyl, aminoethyl, aminopropyl, aminobutyl, hydroxymethyl, hydroxyethyl, hydroxypropyl, hydroxybutyl, methylamino, ethylamino, propylamino, butylamino, acetylamino, propionylamino and methylsulphonylamino radical.

Halogen is to be understood to be fluorine or chlorine, fluorine being preferred.

If, in general formula (I), $R_2$ and $R_3$ are alkyl radicals, then they are to be understood to be straight or branched alkyl chains containing up to 6 carbon atoms, the methyl, ethyl, propyl and butyl radicals being preferred.

If $R_2$ and $R_3$, together with the carbon atom to which they are attached, form a carbocyclic ring, then there are to be understood thereunder rings with three to seven members, the cyclopropane, cyclobutane, cyclopentane and cyclohexane rings being preferred.

If, in general formula (I), $R_4$ is an alkylaminocarbonyl, dialkylaminocarbonyl, alkylcarbonylamino, alkylsulphonylamino, alkylcarbonylhydrazinocarbonyl or alkylsulphonylhydrazinocarbonyl radical, then there are to be understood thereunder straight-chained, branched and cyclic alkyl radicals containing up to 6 carbon atoms.

Preferred in this sense are the methylaminocarbonyl, ethylaminocarbonyl, propylaminocarbonyl, butylaminocarbonyl, dimethylaminocarbonyl, methylethylaminocarbonyl, diethylaminocarbonyl, cyclohexylmethylaminocarbonyl, acetylamino, propionylamino, butylcarbonylamino, methylsulphonylamino, ethylsulphonylamino and propylsulphonylamino radicals.

If, in general formula (I), X is an alkylene radical, then there are to be understood an alkylene radical containing up to 4 carbon atoms, the methylene and ethylene radicals being preferred.

Especially preferred compounds include those of general formula (I) in which $R_1$ is a phenyl radical of general formula (II), wherein $R_5$ is a hydrogen atom or a methanesulphonyloxy, trifluoromethanesulphonyloxy, methanesulphonylamino, trifluoromethanesulphonylamino, methanesulphonylmethylamino, trifluoromethanesulphonylmethyl-amino, methylsulphenylmethyl, methylsulphinylmethyl, methylsulphonylmethyl, aminocarbonyl, aminosulphonyl, methylaminosulphonyl, dimethylaminosulphonyl, acetylamino, methylthio, methylsulphinyl, methylsulphonyl, hydroxyl, methyl, methoxy, propargyloxy, cyanomethyloxy, methoxycarbonylmethyloxy, cyano, chloro, nitro, amino, dimethylamino, trifluoromethyl or 1-imidazolyl radical, $R_6$ is a hydrogen or chlorine atom or a methyl, methoxy or dimethylamino radical, $R_7$ is a hydrogen atom or a methoxy radical or $R_1$ is the pyrrole, furan, thiophene, pyrazole, imidazole, isothiazole, thiazole, oxazole, triazole, tetrazole, thiadiazole, isoxazole, oxadiazole, pyridine, N-oxypyridine, pyrazine, N,N'-dioxypyrazine, pyrimidine, N,N'-dioxypyrimidine, pyridazine, oxazine, thiazine, triazine or tetrazine radical, as well as the methyl-, ethyl-, methoxy-, ethoxy-, methylthio-, ethylthio- and chlorine-substituted derivatives thereof or an indole, indazole, quinoline, isoquinoline, pyrrolidine, piperidine, morpholine, thiomorpholine or naphthyl radical, or $R_1$, for the case in which X is a valency bond, besides the mentioned groups, can also be a hydrogen atom or a methyl, ethyl, propyl, butyl, pentyl, hexyl, propenyl, cyclopentenyl, cyclohexyl, trifluoromethyl, hydroxyl, mercapto, methylthio, amino, acetylamino or formylamino radical, $R_2$ and $R_3$ are the same and are methyl radicals or $R_2$ and $R_3$ together form a cyclopentane ring, $R_4$ is a cyano, aminocarbonyl, amino, formylamino, acetylamino, isopropionylamino, tert.-butylcarbonylamino, trifluoromethylcarbonylamino, methylsulphonylamino, n-propylsulphonylamino, isopropylsulphonylamino, trifluoromethylsulphonylamino, phenylsulphonylamino, methylaminocarbonylamino or acetylaminocarbonylamino radical; X is a valency bond, a methylene radical, an imino group or a carbonylamino group and n is 0 to 1.

The compounds of the general formula (I) can be prepared by known processes, especially advantageous synthesis routes being illustrated in the following:

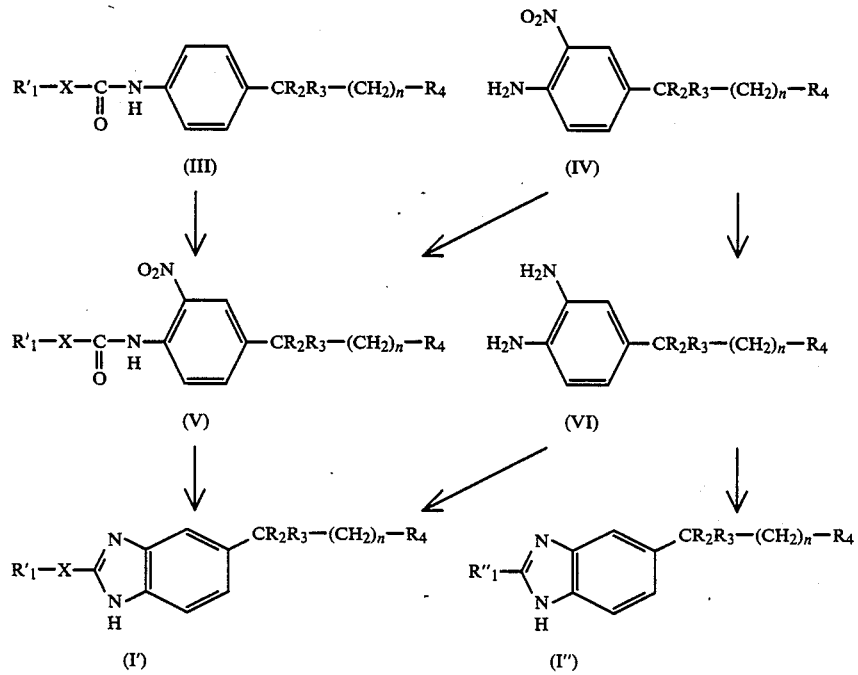

The compounds of the general formula (I'), in which X, $R_2$, $R_3$, $R_4$ and n have the given meanings and $R'_1$ has the meaning given above for $R_1$ with the exception that when X is a valency bond, $R'_1$ is not an amino, hydroxyl or mercapto group, are prepared by either (a) reducing a compound of the general formula (V), in which $R'_1$, X, $R_2$, $R_3$, $R_4$ and n have the given meanings, and cyclising to give a compound of general formula (I'), or (b) reacting a compound of the general formula (VI), in which $R_2$, $R_3$, $R_4$ and n have the above-given meanings, with a compound of the general formula:

in which $R'_1$ and X have the given meanings and Y is either a hydrogen atom, a hydroxyl group or a group which can easily be split off, to give a compound of general formula (I').

Compounds of general formula (I''), in which $R''_1$ is an amino, hydroxyl or mercapto group and $R_2$, $R_3$, $R_4$ and n have the above-given meanings, can be prepared by (c) reacting a compound of general formula (VI), in which $R_2$, $R_3$, $R_4$ and n have the given meanings, with a reagent which transfers the carbonyl, thiocarbonyl or imino group, for example phosgene, thiophosgene, 1,1'-carbonyldiimidazole, a chloroformic acid ester, urea or cyanogen bromide.

The compound of general formula (I) obtained according to the processes a–c or its tautomer can subsequently, if desired, be converted into another compound of the general formula (I) and/or converted into a physiologically acceptable salt of an inorganic or organic acid.

The reduction mentioned in process a is preferably carried out in a solvent or solvent mixture, such as water, methanol, ethanol, glacial acetic acid, ethyl acetate or dimethylformamide, with hydrogen in the presence of a catalyst, such as Raney nickel, platinum or palladium/charcoal, with a metal such as iron, tin or zinc, in the presence of an acid, with a salt, such as ferrous sulphate, stannous chloride, sodium sulphide, sodium hydrogen sulphite or sodium dithionite, or with hydrazine in the presence of Raney nickel at a temperature of from 0° to 100° C. but preferably at ambient temperature. The cyclised compounds of general formula (I') are usually obtained directly.

If desired, the cyclisation can be completed in that, after the reduction, heating is preferably carried out in a solvent or solvent mixture, such as ethanol, isopropanol, glacial acetic acid, benzene, toluene, chlorobenzene, glycol, ethylene glycol dimethyl ether, sulfolan or dimethylformamide, to a temperature of from 50° to 220° C. but preferably to the boiling temperature of the reaction mixture, optionally in the presence of a condensation agent, such as phosphorus oxychloride, thionyl chloride, p-toluenesulphonic acid, hydrochloric acid, sulphuric acid, phosphoric acid or polyphosphoric acid, or optionally also in the presence of a base, such as sodium hydroxide, sodium ethylate or potassium tert.-butylate. The cyclisation can, however, also be carried out without solvents and/or condensation agents.

Amongst the compounds of general formula (VII) mentioned in process b are to be understood aldehydes, carboxylic acids, acid halides, such as acid chlorides, carboxylic acid esters, such as methyl and ethyl esters, and other activated carboxylic acid derivatives, as well as anhydrides.

If the compound of general formula (VII) is an aldehyde, then the reaction takes place with compounds of general formula (VI) under oxidising conditions, preferably in alcoholic medium with heating to reflux in the presence of atmospheric oxygen and catalytic amounts of acid, such as toluenesulphonic acid, or in the presence of atmospheric oxygen and of a catalyst, such as pyrolusite in acidic medium, such as glacial acetic acid, at ambient temperature. It is often advantageous first to convert the aldehyde into a bisulphite adduct by reaction with NaHSO$_3$ which is then further reacted under the conditions just described for the aldehyde.

If the compound of general formula (VII) is a carboxylic acid, then the reaction with a compound of general formula (VI) takes place in the presence of a water-removing agent, preferably in polyphosphoric acid, at a temperature of from 50° to 250° C. and preferably of from 100° to 200° C.

If the compound of general formula (VII) is a carboxylic acid derivative, then the reaction with a compound of general formula (VI) takes place in an inert solvent, preferably in methylene chloride or pyridine. For completion of the cyclisation, heating is subsequently carried out in a solvent or solvent mixture, such as ethanol, isopropanol, glacial acetic acid, benzene, chlorobenzene, glycol, diethylene glycol dimethyl ether, sulfolan or dimethylformamide, to a temperature of from 50° to 250° C. but preferably to the boiling temperature of the solvent or solvent mixture, optionally in the presence of a condensation agent, such as phosphorus oxychloride, thionyl chloride, p-toluenesulphonic acid, hydrochloric acid, sulphuric acid, phosphoric acid or polyphosphoric acid, or optionally also in the presence of a base, such as sodium hydroxide, potassium methylate or potassium tert.-butylate. However, the cyclisation can also be carried out without solvents and/or condensation agents.

The cyclisation of the compounds of general formula (VI) described in process c to give compounds of general formula (II'') is preferably so carried out that phosgene is passed into or thiophosgene is added to a hydrochloric acid solution of compounds of general formula (VI) and left to stand at ambient temperature or compounds of general formula (VI) are heated with cyanogen bromide or urea without a solvent or compounds of general formula (VI) are boiled with 1,1'-carbonyldiimidazole in an inert solvent, such as dioxan.

The compounds of general formula (V), in which $R_1$, $R_2$, $R_3$, $R_4$ and n have the given meanings, needed as starting materials are prepared:

(a) by nitration of compounds of general formula (III) or (b) by reaction of compounds of general formula (IV) with carboxylic acids or carboxylic acid derivatives of the general formula (VIII)

(VIII)

in which $R_1'$ and X have the given meanings and Z is the hydroxyl group or a residue which can easily be split off.

The compounds of general formula (VI), in which $R_2$, $R_3$, $R_4$ and n have the given meanings, needed as starting materials are obtained by reduction of compounds of general formula (IV).

The compounds of general formulae (III) and (IV) are known from the literature or can be obtained by processes known from the literature.

The conversion of compounds of general formula (I) into other compounds of general formula (I) applies, for example, to the following cases:

(a) For the reaction of compounds of general formula (I), in which $R_1$ is an amino, aminoalkyl or a saturated cyclic imino group or is a heterocyclic five- or six-membered ring substituted with an amino group or is a phenyl ring of general formula (II) in which one or more of the substituents $R_5$, $R_6$ and $R_7$ are amino groups and/or in which $R_4$ is an amino group, with carboxylic acids or with activated carboxylic acid derivatives, such as anhydrides or acid halides, to formylamino or alkylcarbonylamino derivatives. The reaction is preferably carried out with carboxylic acids in the presence of a water-removing agent, for example polyphosphoric acid, or of a solvent forming an azeotropic mixture with water, such as benzene or toluene. Reactions with activated carboxylic acid derivatives are preferably carried out in inert solvents, such as methylene chloride or pyridine, at temperatures of from 0° to 250° C. but preferably at the boiling temperature of the solvent.

(b) For the reaction of compounds of general formula (I), in which $R_1$ is an amino, aminoalkyl or a saturated cyclic imino group or $R_1$ is a heterocyclic five- or six-membered ring substituted with an amino group as initially defined or $R_1$ is a phenyl radical of general formula (II) in which one of the substituents $R_5$, $R_6$, $R_7$ is an amino, N-alkylamino or hydroxyl group and/or $R_4$ is an amino group, with a sulphonic acid of the general formula:

$$R_8\text{-}SO_2OH \qquad (IX),$$

in which $R_8$ is an alkyl radical containing up to 3 carbon atoms or a trifluoromethyl radical, or with a reactive derivative thereof, to give compounds of general formula (I), in which the said amino, aminoalkyl, cyclic imino, N-alkylamino or hydroxyl groups are sulphonated.

The reaction is preferably carried out in a solvent or solvent mixture, such as methylene chloride, diethyl ether, tetrahydrofuran, dioxan or benzene, optionally in the presence of an acid-binding agent, such as sodium carbonate, triethylamine or pyridine, whereby the last two can also simultaneously be used as solvent, in the presence of an agent activating the acid or removing water, such as thionyl chloride or phosphorus pentachloride, but preferably with a reactive derivative of a compound of general formula (IX), for example with an anhydride or halide thereof, such as methanesulphonic acid chloride or ethanesulphonic acid chloride, preferably at a temperature of from 0° to 100° C., for example at temperatures of from ambient temperature to 50° C.

(c) For the conversion of compounds of general formula (I), in which $R_1$ is a phenyl radical of general formula (II), in which one of the substituents $R_5$, $R_6$ and $R_7$ is an alkylthio or alkylsulphenylmethyl radical containing up to 3 carbon atoms in the alkyl moiety, into compounds of general formula (I), in which $R_1$ is a phenyl radical and one of the substituents $R_5$, $R_6$ and $R_7$ is an alkylsulphinyl, alkylsulphonyl, alkylsulphinylmethyl or alkylsulphonylmethyl radical.

This oxidation is preferably carried out in a solvent or solvent mixture, for example in water, water/pyridine, acetone, glacial acetic acid, dilute sulphuric acid or trifluoroacetic acid, depending upon the oxidation agent used preferably at a temperature of from −80° to 100° C.

For the preparation of an alkylsulphinyl or alkylsulphinylmethyl compound of general formula (I), the oxidation is preferably carried out with one equivalent of the oxidation agent used, for example with hydrogen peroxide in glacial acetic acid, trifluoroacetic acid or formic acid at 0° to 20° C. or in acetone at 0° to 60° C., with a per acid, such as performic acid, in glacial acetic acid or trifluoroacetic acid, at 0° to 50° C. or with m-chloroperbenzoic acid in methylene chloride or chloroform at −20° to 60° C., with sodium metaperiodate in aqueous methanol or ethanol at −15° to 25° C., with bromine in glacial acetic acid or aqueous acetic acid, with N-bromosuccinimide in ethanol, with tert.-butyl hypochloride in methanol at −80° C. to −30° C., with iodobenzodichloride in aqueous pyridine at 0° to 50° C., with nitric acid in glacial acetic acid at 0° to 20° C., with chromic acid in glacial acetic acid or in acetone at 0° to 20° C. and with sulphuryl chloride in methylene chloride at −70° C., the thioether-chlorine complex thereby obtained preferably being hydrolysed with aqueous ethanol.

For the preparation of an alkylsulphonyl or alkylsulphonylmethyl compound of general formula (I), the oxidation is preferably carried out with one or with two or more equivalents of the oxidation agent used, for example hydrogen peroxide in glacial acetic acid, trifluoroacetic acid or formic acid at 20° to 100° C., or in acetone at 0° to 60° C., with a per acid, such as performic acid, or m-chloroperbenzoic acid in glacial acetic acid, trifluoroacetic acid, methylene chloride or chloroform at a temperature of from 0° to 60° C., with nitric acid in glacial acetic acid at 0° to 20° C., with chromic acid or potassium permanganate in glacial acetic acid, water/sulphuric acid or in acetone or at 0° to 20° C.

(d) For the conversion of compounds of general formula (I), in which $R_1$ is a phenyl radical of general formula (II), in which one of the substituents $R_5$, $R_6$ and $R_7$ is a carboxyl or hydroxysulphonyl group, into compounds of general formula (I), in which one of the substituents $R_5$, $R_6$ and $R_7$ is a carbonyl or sulphonyl group substituted by an amino, alkylamino or dialkylamino group. This takes place by reaction with an amine of the general formula $HNR_9R_{10}$, wherein $R_9$ and $R_{10}$ can be the same or different and are hydrogen atoms or $C_1$-$C_5$-alkyl radicals, or with a reactive derivative hereof. It is advantageous to convert the carboxyl group or hydroxysulphonyl group into a reactive derivative, for example into an ester or an acid chloride, and then to react with the amine $HNR_9R_{10}$.

The reaction is preferably carried out in a solvent or solvent mixture, such as methylene chloride, ethanol, chloroform, carbon tetrachloride, diethyl ether, tetrahydrofuran, dioxan, benzene, toluene, acetonitrile or dimethylformamide, optionally in the presence of an agent activating the acid or removing water, for example in the presence of ethyl chloroformate, thionyl chloride, phosphorus trichloride, phosphorus pentoxide, N',N-dicyclohexylcarbodiimide/N-hydroxysuccinimide, N,N'-carbonyldiimidazole or N,N'-thionyldiimidazole or triphenyl phosphine/carbon tetrachloride, or of an agent activating the amino group, for example phosphorus trichloride, and optionally in the presence of an inorganic base, such as sodium carbonate, or of a tertiary organic base, such as triethylamine or pyridine, which can simultaneously serve as solvent, at a temperature of from −25° to 250° C. but preferably at a temperature of from −10° C. to the boiling temperature of the solvent used. Furthermore, water formed during the reaction can be separated off by azeotropic distillation, for example by heating with toluene on a water separator, or by the addition of a drying agent, such as anhydrous magnesium sulphate or a molecular sieve.

However, the reaction is carried out especially advantageously in a corresponding halide, for example the carboxylic acid or sulphonic acid chloride, and a corresponding amine, whereby these can simultaneously serve as solvent, and at a temperature of from 0° to 50° C.

The reaction conditions just mentioned also apply to the preparation of compounds of general formula (I), in which $R_4$ is an alkylaminocarbonyl or dialkylaminocarbonyl radical, from compounds of general formula (I), in which $R_4$ is a carboxyl group or a reactive derivative hereof.

(e) For the conversion of compounds of general formula (I), in which $R_1$ is a phenyl radical of general formula (II) and one of the substituents $R_5$, $R_6$ and $R_7$ is a cyano group and/or in which $R_4$ is a cyano group, into compounds of general formula (I), in which $R_1$ is a phenyl radical of general formula (II)

and one of the substituents $R_5$, $R_6$ and $R_7$ is an alkoxycarbonyl or aminocarbonyl radical or a carboxyl group, and/or in which $R_4$ is an aminocarbonyl radical.

This alcoholysis and/or hydrolysis is carried out either in the presence of an acid, such as hydrochloric acid, sulphuric acid, phosphoric acid or trichloroacetic acid, or in the presence of a base, such as sodium hydroxide or potassium hydroxide, in a appropriate solvent, such as water, water/methanol, ethanol, water/ethanol, water/isopropanol or water/dioxan, at a temperature of from $-10°$ to $120°$ C., for example at a temperature of from ambient temperature and the boiling temperature of the reaction mixture.

(f) For the conversion of compounds of general formula (I), in which $R_4$ is a cyano group or an aminocarbonyl radical, into those compounds of general formula (I) in which $R_4$ is an amino group. In the case of this reduction, the value of n increases to $n+1$.

This reduction is carried out in an inert solvent by means of lithium alanate or sodium borohydride, in the presence of cobalt chloride, with borane or by catalytic hydrogenation at elevated temperatures and pressures.

(g) For the alkylation of compounds of general formula (I), in which $R_1$ is a phenyl radical of general formula (II), in which one of the substituents $R_5$, $R_6$ and $R_7$ is a hydroxyl or mercapto group, or in which $R_1$ is a heterocyclic ring substituted with a hydroxyl or mercapto group or in which X is a valency bond and $R_1$ is a hydroxyl or mercapto group, the corresponding alkylthio or alkoxy compounds thereby being obtained.

The reaction is preferably carried out in a solvent, such as acetone, diethyl ether, benzene, toluene or dimethylformamide, at a temperature of from $-30°$ to $+100°$ C. and preferably at ambient temperature in the presence of a base, such as potassium carbonate or sodium hydride, and of an alkylation agent, such as an alkyl halide or alkyl sulphate.

(h) For the reduction of compounds of general formula (I), in which $R_1$ is a pyridine ring, into compounds of general formula (I), in which $R_1$ is a piperidine ring. These reductions are preferably carried out in an alcoholic medium in the presence of a catalyst, such as platinum or palladium, by means of hydrogen at normal pressure or slightly elevated pressure and at a temperature of from ambient temperature to $60°$ C.

(i) For the hydrogenation of a vinyl compound ($X=-CH=CH-$) into a corresponding ethyl compound ($X=-CH_2-CH_2-$). The hydrogenation is preferably carried out in a solvent, such as water, water/ethanol, methanol, glacial acetic acid, ethyl acetate or dimethylformamide, preferably with hydrogen in the presence of a hydrogenation catalyst, such as Raney nickel, platinum or palladium/charcoal.

(k) For the oxidation of a five- or six-membered ring with one or more nitrogen atoms to the corresponding N-oxides. The oxidation is preferably carried out with one or more equivalents of the oxidation agent used, for example with hydrogen peroxide in glacial acetic acid, trifluoroacetic acid or in formic acid at $20°-100°$ C. or in acetone at $0°-60°$ C., with a per acid, such as performic acid or m-chloroperbenzoic acid in glacial acetic acid, trifluoroacetic acid, methylene chloride or chloroform at a temperature of from $0°$ to $60°$ C.

(l) For the hydrogenation of compounds of general formula (I), in which $R_1$ is an unsaturated heterocycle, to give compounds of general formula (I), in which $R_1$ is a saturatured heterocycle. This reduction is preferably carried out in an inert solvent, for example water, methanol, ethanol, glacial acetic acid, ethyl acetate or dimethylformamide, with hydrogen in the presence of a hydrogenation catalyst, for example Raney nickel, platinum or palladium.

(m) For the reaction of compounds of general formula (I), in which $R_4$ is an amino group, to give compounds of general formula (I), in which $R_4$ is a dialkylaminocarbonylamino radical. This reaction is preferably carried out with dialkylcaramic acid chlorides in an inert solvent, such as dichloromethane, in the presence of a base, such as triethylamine, at $0°$ to $50°$ C.

Furthermore, the compounds obtained of general formula (I) can subsequently, if desired, be converted into their physiologically acceptable acid-addition salts with inorganic and organic acids. As acids herefor, there can be used, for example, hydrochloric acid, hydrobromic acid, sulphuric acid, phosphoric acid, fumaric acid, succinic acid, tartaric acid, citric acid, lactic acid, maleic acid or methanesulphonic acid.

As already mentioned initially, the new compounds of general formula (I), their tautomers and their physiologically acceptable acid-addition salts display superior pharmacological properties. In particular, they lower the blood pressure and/or have a positive inotropic action and/or influence the thrombocyte function and improve the microcirculation.

For the preparation of pharmaceutical compositions, the compounds of general formula (I) are mixed in known manner with appropriate pharmaceutical carrier substances, aroma, flavouring and colouring materials and formed, for example, into tablets or dragees or, with the addition of appropriate adjuvant materials, are suspended or dissolved in water or in an oil, for example olive oil.

The new compounds of general formula (I) according to the present invention and their salts can be administered enterally or parenterally in liquid or solid form. As injection medium, there is preferably used water which contains the additives usual in the case of injection solutions, such as stabilising agents, solubilising agents or buffers.

Such additives include, for example, tartrate and citrate buffers, ethanol, complex formers (such as ethylenediamine-tetraacetic acid and its non-toxic salts) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycol). Compositions suitable for oral administration can, if desired, contain flavouring and sweetening agents.

The compounds according to the present invention are usually administered in amounts of from 10 to 500 mg. per day, referred to 75 kg. body weight. It is preferred to administer 2 to 3 times a day 1 or 2 tablets with an active material content of 5 to 200 mg. The tablets can also be retarded, in which case only 1 or 2 tablets with 10 to 500 mg. of active material have to be given once per day. The active material can also be given by injection 1 to 8 times per day or by continuous infusion, in which case amounts of 5 to 200 mg./day normally suffice.

Especially preferred in the meaning of the present invention, apart from the compounds mentioned in the Examples, are the following compounds and the tautomers thereof:

5-(2-formylaminomethylpropan-2-yl)-2-(4-pyridazinyl)-benzimidazole
5-(2-formylaminomethylpropan-2-yl)-2-(2-pyrazinyl)-benzimidazole
5-(2-formylaminomethylpropan-2-yl)-2-(2-hydroxypyridin-4-yl)-benzimidazole
5-(2-formylaminomethylpropan-2-yl)-2-(3-hydroxypyridin-4-yl)-benzimidazole
5-(2-formylaminomethylpropan-2-yl)-2-(2,6-dihydroxypyridin-4-yl)-benzimidazole
5-(2-formylaminomethylpropan-2-yl)-2-(2-chloropyridin-4-yl)-benzimidazole
5-(2-formylaminomethylpropan-2-yl)-2-(2-methylpyridin-5-yl)-benzimidazole
5-(2-formylaminomethylpropan-2-yl)-2-(5-n-butylpyridin-2-yl)-benzimidazole
5-(2-formylaminomethylpropan-2-yl)-2-(6-hydroxypyrididazin-3-yl)-benzimidazole
5-(2-formylaminomethylpropan-2-yl)-2-[2-(3-pyridinyl)ethenyl]-benzimidazole
5-(2-formylaminomethylpropan-2-yl)-2-[2-(3-pyridinyl)ethyl]-benzimidazole
5-(2-formylaminomethylpropan-2-yl)-2-(2-pyrrolyl)-benzimidazole
5-(2-formylaminomethylpropan-2-yl)-2-(3-thienyl)benzimidazole
5-(2-formylaminomethylpropan-2-yl)-2-thenylbenzimidazole
5-(2-formylaminomethylpropan-2-yl)-2-(4-thiazolyl)-benzimidazole
5-(2-formylaminomethylpropan-2-yl)-2-(5-isoxazolyl)-benzimidazole
5-(2-formylaminomethylpropan-2-yl)-2-(2-methyloxazol-4-yl)-benzimidazole
5-(2-formylaminomethylpropan-2-yl)-2-(5-methylpyrazol-3-yl)-benzimidazole
5-(2-formylaminomethylpropan-2-yl)-2-(1,2,4-triazol-3-yl)-benzimidazole
5-(2-formylaminomethylpropan-2-yl)-2-[(5-carboxy)-1,2,3-triazol-4-yl]-benzimidazole
5-(2-formylaminomethylpropan-2-yl)-2-[(5-methoxycarbonyl)-1,2,3-triazol-4-yl]-benzimidazole
5-(2-formylaminomethylpropan-2-yl)-2-(1,2,3-thiadiazol-4-yl)-benzimidazole
5-(2-formylaminomethylpropan-2-yl)-2-(1,2,3-thiadiazol-5-yl)-benzimidazole
5-(2-formylaminomethylpropan-2-yl)-2-(1,3,4-thiadiazol-2-yl)-benzimidazole
5-(2-formylaminomethylpropan-2-yl)-2-[(5-methylthio)-1,3,4-oxadiazol-2-yl]-benzimidazole
5-(2-formylaminomethylpropan-2-yl)-2-(3-quinolinyl)-benzimidazole
5-(2-formylaminomethylpropan-2-yl)-2-(2-indolyl)benzimidazole
5-(2-formylaminomethylpropan-2-yl)-2-(1-naphthylmethyl)benzimidazole
5-(2-formylaminomethylpropan-2-yl)-2-phenylbenzimidazole
5-(2-formylaminomethylpropan-2-yl)-2-(2-methoxyphenyl)benzimidazole
5-(2-formylaminomethylpropan-2-yl)-2-(2-methoxy-4-methylsulphinylphenyl)-benzimidazole
5-(2-formylaminomethylpropan-2-yl)-2-(2-methoxy-4-methylsulphonylphenyl)-benzimidazole
5-(2-formylaminomethylpropan-2-yl)-2-[4-(1-imidazolyl)phenyl]-benzimidazole
5-(2-formylaminomethylpropan-2-yl)-2-(4-chlorophenyl)benzimidazole
5-(2-formylaminomethylpropan-2-yl)-2-(4-trifluoromethylphenyl)-benzimidazole
5-(2-formylaminomethylpropan-2-yl)-2-(2-acetamidophenyl)benzimidazole
5-(2-formylaminomethylpropan-2-yl)-2-(4-tert.-butylphenyl)-benzimidazole
5-(2-formylaminomethylpropan-2-yl)-2-n-propylbenzimidazole
5-(2-formylaminomethylpropan-2-yl)-2-isopropylbenzimidazole
5-(2-formylaminomethylpropan-2-yl)-2-isopropenylbenzimidazole
5-(2-formylaminomethylpropan-2-yl)-2-tert.-butylbenzimidazole
5-(2-formylaminomethylpropan-2-yl)-2-cyclopropylbenzimidazole
5-(2-formylaminomethylpropan-2-yl)-2-(1-cyclopentenyl)benzimidazole
5-(2-formylaminomethylpropan-2-yl)-2-(2-carboxyethyl)benzimidazole
5-(2-formylaminomethylpropan-2-yl)-2-methoxymethylbenzimidazole
5-(2-formylaminomethylpropan-2-yl)-2-(3-aminopropyl)benzimidazole
5-(2-formylaminomethylpropan-2-yl)-2-mercaptobenzimidazole
5-(2-formylaminomethylpropan-2-yl)-2-methylthiobenzimidazole
5-(2-formylaminomethylpropan-2-yl)-2-aminobenzimidazole
5-(2-formylaminomethylpropan-2-yl)-2-(4-pyridinylamino)benzimidazole
5-(2-formylaminomethylpropan-2-yl)-2-(2-thiazolylamino)benzimidazole
5-(2-formylaminoethyl)-2-(4-pyridinyl)-benzimidazole
5-(1-formylaminopropan-2-yl)-2-(4-pyridinyl)-benzimidazole
5-(1-formylaminobutan-2-yl)-2-(4-pyridinyl)-benzimidazole
5-(1-formylamino-2-methylbutan-2-yl)-2-(4-pyridinyl)-benzimidazole
5-[2-(tert.-butylcarbonylaminomethyl)-propan-2-yl]-2-(4-methoxyphenyl)-benzimidazole
5-[2-(trifluoromethylcarbonylaminomethyl)-propan-2-yl]-2-(4-pyridinyl)-benzimidazole
5-[2-(methylsulphonylaminomethyl)-propan-2-yl]-2-(2-methoxy-4-methylsulphonylphenyl)-benzimidazole
5-[2-(n-propylsulphonylaminomethyl)-propan-2-yl]-2-(4-methoxyphenyl)-benzimidazole
5-[2-(isopropylsulphonylaminomethyl)-propan-2-yl]-2-(4-methoxyphenyl)-benzimidazole
5-[2-(trifluoromethylsulphonylaminomethyl)-propan-2-yl]-2-(4-methoxyphenyl)-benzimidazole
5-[2-(phenylsulphonylaminomethyl)-propan-2-yl]-2-(4-methoxyphenyl)-benzimidazole
5-[2-(methylaminocarbonylaminomethyl)-propan-2-yl]-2-(4-pyridinyl)-benzimidazole 5-[2-(acetylaminocarbonylaminomethyl)-propan-2-yl]-2-(4-pyridinyl)-benzimidazole
5-(2-methyl-2-formylaminopropan-2-yl)-2-(4-methoxyphenyl)-benzimidazole
5-(3-formylaminopropyl)-2-(4-methoxyphenyl)-benzimidazole
5-(2-formylaminopropyl)-2-(4-pyridinyl)-benzimidazole
5-(2-methyl-2-formylaminopropan-2-yl)-2-(4-pyridinyl)benzimidazole
5-(3-formylaminopropyl)-2-(4-pyridinyl)-benzimidazole
5-(2-methyl-3-formylaminopropyl)-2-(4-pyridinyl)benzimidazole
5-(1-methyl-4-methylaminocarbonylbutyl)-2-(4-pyridinyl)benzimidazole
5-(1-methylaminocarbonylpropan-2-yl)-2-(4-pyridinyl)-benzimidazole
5-(1-aminocarbonylpropan-2-yl)-2-(4-pyridinyl)benzimidazole
5-[1-(N-cyclohexyl-N-methylaminocarbonyl)-propan-2-yl]-2-(4-pyridinyl)-benzimidazole
5-(2-cyanopropan-2-yl)-2-(2-methoxy-2-methylthiophenyl)benzimidazole
5-(2-cyanopropan-2-yl)-2-(2-methoxy-4-methylsulphinylphenyl)-benzimidazole
5-(2-cyanopropan-2-yl)-2-(2-methoxy-4-methylsulphonylphenyl)-benzimidazole
5-(2-aminocarbonylpropan-2-yl)-2-(4-methoxyphenyl)-benzimidazole
5-[2-[(3,3-dimethyloxindol-5-yl)-methylaminomethyl]-propan-2-yl]-2-(4-pyridinyl)-benzimidazole
5-(1-methyl-2 methylaminocarbonylethyl)-2-(4-pyridinyl)benzimidazole
5-(2-formylaminomethylpropan-2-yl)-2-(5-pyrimidinyl)benzimidazole.

The following Examples are given for the purpose of illustrating the present invention:

EXAMPLE 1

5-(2-Aminomethylprop-2-yl)-2-(4-pyridinyl)-benzimidazole (a) 63.7 g. 4-(2-cyanoprop-2-yl)-aniline in 1 liter toluene are mixed with 50 ml. acetic anhydride. After 30 minutes, the reaction mixture is cooled to ambient temperature, stirred with an aqueous solution of sodium bicarbonate and the organic phase is separated off and evaporated to dryness in a vacuum. The residue is taken up in toluene, crystals are filtered off with suction and dried in the air to give 73.6 g. (91% of theory) 4-(2-cyanoprop-2-yl)-acetanilide; m.p. 113°–114° C.

(b) 84.3 g. 4-(2-cyanoprop-2-yl)-acetanilide are hydrogenated in 400 ml. ethanol in the presence of 300 ml. liquid ammonia and 5 g. Raney nickel at 90° C. and 50 bar hydrogen pressure for 6 hours at 90° C. After filtering off the catalyst with suction and evaporating the filtrate, there are obtained, after crystallisation from toluene, 72.5 g. (84% of theory) 4-(2-aminomethylprop-2-yl)-acetanilide as colourless crystals; m.p. 97°–101° C.

(c) To 72.5 g. 4-(2-aminomethylprop-2-yl)-acetanilide in 400 ml. dichloromethane are added dropwise, with ice cooling, 36.5 ml. acetic anhydride. Subsequently, the reaction mixture is stirred for 1 hour at ambient temperature and evaporated in a vacuum and the residue is digested with ethyl acetate, filtered off with suction and washed with ethyl acetate to give 82.0 g. (94% of theory) N,N′-diacetyl-4-(2-aminomethylprop-2-yl)-aniline as colourless crystals; m.p. 171°–172° C.

(d) To 125 g. N,N′-diacetyl-4-(2-aminomethylprop-2-yl)aniline in 315 ml. concentrated sulphuric acid is added dropwise at 0° C. a mixture of 39 ml. 65% nitric acid (d=1.4) and 59 ml. concentrated sulphuric acid. The reaction mixture is further stirred for 30 minutes at ambient temperature, poured on to ice and extracted with dichloromethane. The organic phase is shaken with aqueous sodium bicarbonate solution and the organic phase is evaporated in a vacuum. The viscous residue is taken up in 200 ml. ethyl acetae, mixed with diethyl ether up to the commencement of turbidity and left to crystallise. The crystals are filtered off with suction and washed with ethyl acetate/diethyl ether (2:1 v/v) to give 122 g. (83% of theory) N,N′-diacetyl-4-(2-aminomethylprop-2-yl)-2-nitroaniline as pale yellow crystals; m.p. 138°–139° C.

(e) To 25 g. potassium hydroxide in 1 liter methanol are added 122 g. N,N′-diacetyl-4-(2-aminomethylprop-2-yl)-2-nitroaniline and stirred for 1 hour at ambient temperature. It is then neutralised with acetic acid, evaporated to dryness in a vacuum, the residue digested with water and the crystals are filtered off with suction, then washed with water and dried in the air to give 101 g. (97% of theory) 4-(2-acetamidomethylprop-2-yl)-2-nitroaniline as yellow crystals; m.p. 132°–134° C.

(f) 12.5 g. 4-(2-Acetamidomethylprop-2-yl)-2-nitroaniline are hydrogenated in the presence of 1 g. 10% palladium on charcoal at normal pressure and ambient temperature. After 3.6 liters of hydrogen have been taken up, the catalyst is filtered off with suction and the filtrate evaporated in a vacuum to give 11 g. (100% of theory) 4-(2-acetamidomethylprop-2-yl)-1,2-diaminobenzene as brownish oil which is used without further purification.

(g) To 22.1 g. 4-(2-acetamidomethylprop-2-yl)-1,2-diaminobenzene and 42 ml. triethylamine in 500 ml. dichloromethane are added, while cooling with ice water, 27 g. isonicotinic acid chloride hydrochloride. Stirring is continued at ambient temperature until the reaction of the diamine is complete (thin layer chromatography, silica gel, dichloromethane:methanolic ammonia=10:1 v/v). It is shaken with water and the organic phase is separated off and evaporated to dryness in a vacuum. The residue (24.3 g.) is taken up in 200 ml. ethanol, mixed with 60 ml. concentrated hydrochloric acid and boiled under reflux for 3 days. It is evaporated to dryness in a vacuum, the residue is digested with aqueous ammonia solution at pH=6, 50 ml. dichloromethane are added thereto, filtered off with suction and then washed with iced water and dichloromethane to give 14.1 g. of colourless crystals which are purified by column chromatography (column: diameter 6 cm., length 40 cm., filled with 1 liter silica gel, elution agent dichloromethane:methanolic ammonia 15:1 v/v). After combining the appropriate fractions, removing the elution agent in a vacuum and triturating with ethyl acetate, there are obtained 9.2 g. of the title compound as colourless crystals; m.p. 199°–202° C. 2.7 g. thereof are recrystallised from dioxan to give 2.3 g. of colourless crystals; m.p. 203°–204° C.

EXAMPLE 2

5-(2-Formylaminomethylprop-2-yl)-2-(4-pyridinyl)benzimidazole 9.1 g. 5-(2-Aminomethylprop-2-yl)-2-(4-pyridinyl)-benzimidazole are dissolved in 10 ml. formic acid and evaporated in a vacuum. The residue is heated to the boil for 2 hours with 100 ml. toluene on a water separator. After evaporating to dryness in a vacuum, the residue is taken up in a mixture of dichloromethane and methanol (5:2 v/v), mixed with aqueous ammonia and triturated until crystallisation. The crystals are filtered off with suction and then washed with water and dichloromethane to give 9.4 g. of colourless crystals which are recrystallised from water/ethanol (2:1 v/v). There are obtained 8.7 g. (86% of theory) of the title compound which, per mole, contains ⅓ mole of water. The compound melts at 115°–121° C. with the giving off of the water of crystallisation, again crystallises and then again melts at 227°–228° C.

EXAMPLE 3

By reaction of the 4-(2-acetamidomethylprop-2-yl)-1,2-diaminobenzene prepared in Example 1f with the said acid chlorides according to the procedure of Example 1 g, there are obtained the following compounds:

(a) by reaction with 2-pyridinecarbonyl chloride, there is obtained 5-(2-aminomethylprop-2-yl)-2-(2-pyridinyl)benzimidazole in 87% yield as an oil.

(b) by reaction with 4-pyridylacetic acid chloride, there is obtained 5-(2-aminomethylprop-2-yl)-2-(4-pyridinylmethyl)-benzimidazole in 91% yield.

(c) by reaction with 4-quinolinecarbonyl chloride, there is obtained 5-(2-aminomethylprop-2-yl)-2-(4-quinolinyl)benzimidazole in 72% yield.

(d) by reaction with 6-chloronicotinic acid chloride, there is obtained 5-(2-aminomethylprop-2-yl)-2-(6-hydroxypyridin-3-yl)-benzimidazole in 84% yield.

(e) by reaction with 2-chloro-6-methylnicotinic acid chloride, there is obtained 5-(2-aminomethylprop-2-yl)-2-(2-hydroxy-6-methylpyridin-3-yl)-benzimidazole in 35% yield.

(f) by reaction with 3,4-dimethoxybenzoic acid chloride, there is obtained 5-(2-aminomethylpropan-2-yl)-(3,4-dimethoxyphenyl)-benzimidazole in 11% yield.

(g) by reaction with 2-methoxy-4-chlorobenzoic acid chloride, there is obtained 5-(2-aminomethylpropan-2-yl)-2-(2-methoxy-4-chlorophenyl)-benzimidazole in 75% yield.

EXAMPLE 4

The amines obtained in Example 3 are formylated analogously to the procedure in Example 2 to give:

(a) from 10.2 g. of the amine prepared according to Example 3a, after reaction with 10 g. N-cyclohexylsulphamic acid in ethyl acetate, in 60% yield 5-(2-formylaminomethylprop-2-yl)-2-(4-pyridinyl)-benzimidazole as cyclaminate; m.p. 170° C. (decomp.) after crystallisation from water.

(b) from 3.2 g. of the amine prepared according to Example 3b, 1.9 g. 5-(2-formylaminomethylprop-2-yl)-2-(4-pyridinylmethyl)-benzimidazole as beige crystals (m.p. 141°–148° C.) which, for purification, are dissolved in water-saturated ethyl acetate, filtered off with suction from slightly insoluble components and heated to the boil on a water separator. After cooling, there is thus obtained 1.2 g. (34% of theory) of beige crystals; m.p. 153°–156° C.

(c) from 14.5 g. of the amine prepared in Example 3c, 10.0 g. 5-(2-formylaminomethylprop-2-yl)-2-(4-quinolinyl)-benzimidazole as colourless crystals (m.p. 183°–185° C.) which, for purification, are extracted from a socket through a little silica gel with 200 ml. acetone. There are thus obtained 7.6 g. (48% of theory) of colourless crystals; m.p. 186°–189° C.

(d) from 10.5 g. of the amine prepared in Example 3d, 5.6 g. (49%) 5-(2-formylaminomethylprop-2-yl)-2-(6-hydroxypridin-3-yl)-benzimidazole which, after recrystallising twice from water/ethanol, is obtained as colourless crystals; m.p. 211°–215° C.

(e) from 4.4 g. of the amine prepared in Example 3e, 4.5 g. 5-(2-formylaminomethylprop-2-yl)-2-(2-hydroxy-6-methoxypyridin-3-yl)-benzimidazole which is obtained as oil.

(f) from 0.6 g. of the amine prepared in Example 3f, 0.5 g. 5-(2-formylaminomethylpropan-2-yl)-2-(3,4-dimethoxyphenyl)-benzimidazole which, after column chromatographic separation (silica gel; dichloromethanemethanol 80:20 v/v) has an m.p. of 287°–288° C.

(g) from 4.9 g. of the amine prepared in Example 3g, 1.0 g. 5-(2-formylaminomethylpropan-2-yl)-2-(methoxy-4-chlorophenyl)-benzimidazole; m.p. 156°–157° C. after recrystallisation from ethyl acetate (h) from 1.5 g. of the amine prepared in Example 43, 0.5 g. 5-(2-formylaminopropan-2-yl)-2-(2-furyl)-benzimidazole; m.p. 130°–135° C.

(i) from 1.9 g. of the amine prepared in Example 44, 0.7 g. 5-(2-formylaminomethylpropan-2-yl)-2-(thienyl)-benzimidazole; m.p. 157°–159° C.

(j) from 2.6 g. of the 5-(2-aminomethylpropan-2-yl)-2-(2-methoxy-4-methylthiophenyl)-benzimidazole prepared in Example 34, 2.4 g. 5-(2-formylaminomethylpropan-2-yl)-2-(2-methoxy-4-methylthiophenyl)-benzimidazole which, after crystallisation from ethanol/water (4:1 v/v) is obtained as a hydrate; m.p. 122°–124° C.

(k) from 3.0 g. of the amine prepared in Example 41, 2.2 g. 5-(2-formylaminomethylpropan-2-yl)-2-phenyl-benzimidazole as a hard foam with the melting range of 98°–110° C.

(l) from 3.3 g. of the amine prepared in Example 42, 0.6 g. 5-(2-formylaminomethylpropan-2-yl)-2-(4-hydroxyphenyl)-benzimidazole as an oil.

The following compounds are prepared analogously to Example 4:

5-(2-formylaminomethylpropan-2-yl)-2-(1,2,5-thiadiazol-3-yl)-benzimidazole 5-(2-formylaminomethylpropan-2-yl)-2-[(3,3-dimethyl-2-oxindol-5-yl)-methyl]-benzimidazole 5-(2-formylaminomethylpropan-2-yl)-2-(4-dimethylaminophenyl)-benzimidazole 5-(2-formylaminomethylpropan-2-yl)-2-(4-hydroxy-3,5-dimethoxy-phenyl)-benzimidazole 5-(2-formylaminopropan-2-yl)-2-(2-phenylethenyl)-benzimidazole 5-(2-formylaminomethylpropan-2-yl)-2-benzimidazole 5-(2-formylaminomethylpropan-2-yl)-2-(1-propan-1-yl)-benzimidazole 5-(2-formylaminomethylpropan-2-yl)-2-hexylbenzimidazole 5-(2-formylaminomethylpropan-2-yl)-2-cyclohexylbenzimidazole 5-(2-formylaminomethylpropan-2-yl)-2-(2-ethoxycarbonylethyl)-benzimidazole 5-(2-formylaminoethylpropan-2-yl)-2-hydroxybenzimidazole 5-(2-formylaminomethylpropan-2-yl)-2-(4-methoxyphenylamino)-benzimidazole 5-(2-formylaminopropan-2-yl)-2-(4-pyridinyl)-benzimidazole 5-(2-formylamino-2-methylpropan-2-yl)-2-(4-methoxyphenyl)-benzimidazole 5-(2-formylaminopropyl-2-(4-methoxyphenyl)-benzimidazole 5-(2-formylaminomethylpropan-2-yl)-2-(4-methoxyphenyl)-benzimidazole 5-(2-formylaminomethylpropan-2-yl)-2-phenylbenzimidazole 5-(2-formylaminomethylpropan-2-yl)-2-(4-hydroxyphenyl)-benzimidazole

EXAMPLE 5

5-(2-Aminomethylprop-2-yl)-2-(3-pyridinyl)-benzimidazole (a) 6.3 g. 4-(2-Acetamidomethylprop-2-yl)-2-nitroaniline, the preparation of which is described in Example 1e, are placed in 50 ml. dry pyridine, cooled with ice water and 4.9 g. nicotinic acid chloride hydrochloride introduced portionwise, the temperature being maintained below +15° C. After 2 hours at ambient temperature, the reaction mixture is diluted with ice water to its threefold volume and the crystals are filtered off with suction and washed with water to give 8.2 g. (96% of theory) 4-(2-acetamidomethylprop-2-yl)-2-nitro-1-nicotinoylaminobenzene as pale yellow crystals; m.p. 194°–196° C.

(b) 8.2 g. 4-(2-Acetamidomethylprop-2-yl)-2-nitro-1-nicotinoylaminobenzene are hydrogenated in 100 ml. methanol in the presence of 0.8 g. 10% palladium on charcoal at normal pressure and ambient temperature. After 1.5 liters of hydrogen have been taken up, the reaction mixture is filtered and the filtrate evaporated in a vacuum. The residue (7.8 g.) is mixed with 100 ml. ethanol and 30 ml. concentrated hydrochloric acid and boiled under reflux for 3 days.

After evaporating in a vacuum, the residue is taken up in a little water, rendered alkaline with aqueous sodium hydroxide solution and extracted with a mixture of dichloromethane:methanol (10:1 v/v). The organic phase is dried, filtered and evaporated in a vacuum to give 4.4 g. (69% of theory) of the title compound as a brittle mass.

EXAMPLE 6

4-(2-Aminomethylprop-2-yl)-2-(4-methoxyphenyl)-benzimidazole

By the reaction of 10.0 g. 4-(2-acetamidomethylprop-2-yl)-2-nitroaniline, the preparation of which is described in Example 1e, with 7.5 g. anisic acid chloride analogously to the procedure of Example 5a, there is obtained 14.3 g. (93% of theory) 4-(2-acetamidomethylprop-2-yl)-2-nitro-1-(4-methoxyphenylcarbonylamino)-benzene as yellow crystals; m.p. 124°–126° C. Analogously to the procedure in Example 5b, the title compound is obtained therefrom in 98% yield as hydrochloride; m.p. 328°–331° C.

EXAMPLE 7

The amines obtained in Examples 5 and 6 are formylated analogously to Example 2, there being obtained:

(a) from 4.4 g. of the amine prepared in Example 5, 2.2 g. (45% of theory) 5-(2-formylaminomethylprop-2-yl)-2-(3-pyridinyl)-benzimidazole as a hard foam with a melting range of 60°–120° C.

(b) from 11.8 g. of the hydrochloride of the amine prepared in Example 6, 9.8 g. 5-(2-formylaminomethylprop-2-yl)-2-(4-methoxyphenyl)-benzimidazole as colourless crystals (m.p. 165°–170° C.) which, for purification, are dissolved in hot acetone and ethyl acetate added up to the commencement of turbidity to give 6.1 g. (47% of theory) of colourless crystals; m.p. 167°–169° C.

EXAMPLE 8

5-(2-Aminomethylprop-2-yl)-2-benzylbenzimidazole (a) 115 g. 4-(2-cyanoprop-2-yl)-1-nitrobenzene are hydrogenated in 600 ml. ethanol in the presence of 500 ml. liquid ammonia and 5 spoonfuls of Raney nickel at a pressure of 120 bar hydrogen and a temperature of 90° C. for 6 hours. After filtering off with suction, the filtrate is evaporated in a vacuum to give 96 g. 4-(2-aminomethylprop-2-yl)-aniline as an oil.

(b) To 109 ml. acetic acid anhydride is added dropwise 55 ml. formic acid. The mixture is heated for 15 minutes to 50° C. and then cooled to ambient temperature. This solution is added dropwise to 72.3 g. 4-(2-aminomethylprop-2-yl)-aniline in 1 liter dichloromethane, with stirring and ice cooling. After stirring for 30 minutes at ambient temperature, it is mixed with sodium carbonate solution and the organic phase is separated off and evaporated in a vacuum. The residue is taken up in dichloromethane and the crystals are filtered off with suction and then washed to give 43.7 g. (45% of theory) N,N'-diformyl-4-(aminomethylprop-2-yl)-aniline as colourless crystals; m.p. 138°–140°° C.

(c) Into 195 ml. 96% nitric acid (d=1.5), are introduced portionwise, with stirring and cooling, 43.0 g. N,N'-diformyl-4-(aminomethylprop-2-yl)-aniline so that the temperature is kept at 0° C. After stirring for 30 minutes at this temperature, it is poured on to 1.5 kg. of ice, immediately neutralised by the addition of 400 ml. potassium carbonate in 2 liters of water and extracted with a mixture of dichloromethane:methanol (20:1 v/v). The organic phase is dried with anhydrous magnesium sulphate, filtered and evaporated in a vacuum. The residue is purified by column chromatography (2 l. silica gel, ethyl acetate as elution agent). After combination of the appropriate fractions and removal of the elution agent in a vaccum, there are obtained 9.3 g. (18% of theory) N,N'-diformyl-2-(2-aminomethylprop-2-yl)-2-nitroaniline as yellow crystals; m.p. 90°–95° C.

(d) 40 ml. methanol are saturated at 20° C. with ammonia and 9.3 g. N,N'-diformyl-4-(2-aminomethylprop-2-yl)-2-nitroaniline dissolved therein. After 20 hours, it is evaporated in a vacuum and the residue is taken up in dichloromethane and shaken out twice with water. The organic phase is dried, filtered and evaporated in a vacuum to give 9.2 g. of yellow crystals. A sample thereof is recrystallised from toluene/ethyl acetate (2:1 v/v) to give 4-(2-formylaminomethylprop-2-yl)-2-nitroaniline; m.p. 113°–115° C.

(e) To 4.6 g. 4-(2-formylaminomethylprop-2-yl)-2-nitroaniline in 20 ml. anhydrous pyridine are added dropwise, while cooling with ice water, 3.3 g. phenacetyl chloride. The reaction mixture is stirred for one hour at ambient temperature, dichloromethane and ice are added thereto, acidified with hydrochloric acid to pH=1 and the organic phase is separated off and the solvent removed in a vacuum. The residue is purified by column chromatography (diameter 6 cm., length 40 cm., filled with 800 ml. silica gel, elution agent: ethyl acetate). Appropriate fractions are combined and the elution agent removed in a vacuum.

The residue (5.3 g.; 77% of theory) is hydrogenated in 100 ml. methanol in the presence of 0.5 g. 10% palladium on charcoal at normal pressure and ambient temperature. After 950 ml. of hydrogen have been taken up, it is filtered with suction and the filtrate is evaporated in a vacuum. The residue (4.6 g.) is boiled under reflux in 100 ml. ethanol and 10 ml. concentrated hydrochloric acid for 1 hour. After evaporating in a vacuum, the residue is rendered alkaline with aqueous ammonia solution and extracted with dichloromethane. The organic phase is dried, filtered and evaporated in a vacuum to give 4.1 g. of the title compound (42% of theory).

EXAMPLE 9

From 4.2 g. 4-(2-formylaminomethylprop-2-yl)-2-nitroaniline, prepared in Example 8d, there are obtained, by reaction with 2-methoxy-5-methylthiobenzoic acid chloride (4.2 g.) analogously to Example 8e, 4.9 g. (66% of theory) 4-(2-formylaminomethylprop-2-yl)-2-nitro-1-(2-methoxy-5-methylthiobenzoylamino)-benzene as yellowish crystals; m.p. 151°-157° C. By further reaction analogously to Example 8e, there are obtained therefrom 4.0 g. (98% of theory) 5-(2-aminomethylprop-2-yl)-2-(2-methoxy-5-methylthiophenyl)-benzimidazole.

EXAMPLE 10

The amines obtained in Examples 8 and 9 are formylated analogously to Example 2 and there are obtained (a) from 4.1 g of the amine obtained in Example 8, 2.7 g. 5-(2-formylaminomethylprop-2-yl)-2-benzylbenzimidazole (m.p. 120°-127° C.) which is recrystallised from acetone with fullers' earth treatment to give 1.7 g (38% of theory) of colourless crystals; m.p. 128°-130° C.

(b) from 4.4 g. of the amine obtained in Example 9, 4.7 g. 5-(2-formylaminomethylprop-2-yl)-2-(2-methoxy-5-methylmercaptophenyl)-benzimidazole; m.p. 182°-185° C.

EXAMPLE 11

5-(1-Aminomethylcyclopentyl)-2-(4-pyridinyl)-benzimidazole (a) Analogously to Example 8a, from 23 g. 4-(1-cyanocyclopentyl)-1-nitrobenzene, there are obtained 18.7 g. (93% of theory) 4-(1-aminomethylcyclopentyl)-aniline as a yellowish oil.

(b) There are obtained therefrom, analogously to Example 1c, 20.3 g. (75% of theory) N,N'-diacetyl-4-(1-aminomethylcyclopentyl)-aniline as colourless crystals; m.p. 152°-153° C.

(c) There are obtained therefrom, analogously to Example 1d, 17.5 g. (74% of theory) N,N'-diacetyl-4-(1-aminomethylcyclopentyl)-2-nitroaniline as yellowish crystals; m.p. 154°-156° C.

(d) There are obtained therefrom, analogously to Example 1e, 14.2 g. (93% of theory) 4-(1-acetylaminomethylcyclopentyl)-2-nitroaniline as yellow crystals; m.p. 129°-133° C.

(e) From 7.2 g of this compound and 6.1 g. isonicotinoyl chloride hydrochloride, there are obtained, analogously to Example 8e, 8.2 g. (83% of theory) 4-(1-acetylaminomethylcyclopentyl)-2-nitro-1-isonicotinoylaminobenzene (m.p. 158°-160° C.) and, by further reaction analogously to Example 8e, 5.0 g. (81% of theory) of the title compound as a yellowish oil.

EXAMPLE 12

The amine obtained in Example 11 is formylated analogously to Example 2 to give 5.0 g. 5-(1-formylaminomethylcyclopentyl)-2-(4-pyridinyl)-benzimidazole (m.p. 214°-217° C.) which is recrystallised from dioxan:water (2:1 v/v) to give 2.9 g. (54% of theory) of yellow crystals; m.p. 215°-217° C.

EXAMPLE 13

5-(1-Cyanocyclopentyl)-2-(4-pyridinyl)-benzimidazole (a) 45.0 g. 4-(1-Cyanocyclopentyl)-1-nitrobenzene are hydrogenated in 700 ml. methanol in the presence of 2 g. 10% palladium on active charcoal. After filtering and removing the solvent in a vacuum, there are obtained 36.3 g. (94% of theory) 4-(1-cyanocyclopentyl)-aniline as yellowish crystals; m.p. 83°-86° C.

(b) 36.3 g. 4-(1-Cyanocyclopentyl)-aniline in 400 ml. toluene are mixed with 21 ml. acetic anhydride. After 40 minutes, the reaction mixture is cooled to ambient temperature, stirred with aqueous sodium bicarbonate solution and the organic phase is separated off, dried with anhydrous sodium sulphate, filtered and the filtrate evaporated in a vacuum. The residue is digested with a little cold toluene and filtered off with suction to give 35.3 g. (79% of theory) 4-(1-cyanocyclopentyl)-acetanilide; m.p. 111°-113° C.

(c) To a clear solution of 35.3 g. 4-(1-cyanocyclopentyl)-acetanilide in 95 ml. concentrated sulphuric acid is added dropwise at 0° C. a mixture of 7 ml. 65% nitric acid (d=1.4) and 17 ml. concentrated sulphuric acid. After further stirring for 30 minutes at ambient temperature, it is poured on to ice and extracted with dichloromethane. Undissolved components are filtered off with suction, the organic phase is extracted with aqueous sodium bicarbonate solution and the organic phase is dried with anhydrous sodium sulphate, filtered and the solvent removed in a vacuum. The residue is purified by column chromatography (length 50 cm., diameter 6.5 cm.; silica gel, elution agent: dichloromethane) to give 10.5 g. (29% of theory) 4-(1-cyanocyclopentyl)-2-nitroaniline as yellow crystals; m.p. 125°-128° C.

(d) 10.5 g. 4-(1-Cyanocyclopentyl)-2-nitroaniline are hydrogenated in 180 ml. methanol in the presence of 0.5 g. 10% palladium on active charcoal at normal pressure and ambient temperature. After 1.3 liters of hydrogen have been taken up, the reaction mixture is filtered off with suction and the filtrate evaporated in a vacuum to give 9.1 g. (100% of theory) 4-(1-cyanocyclopentyl)-1,2-diaminobenzene as a yellow oil.

(e) Analogously to the procedure in Example 1g, 4.5 g. 4-(1-cyanocyclopentyl)-1,2-diaminobenzene are reacted with 6.0 g. isonicotinic acid chloride hydrochloride to give 5.7 g. of the title compound as the hydrochloride salt which is recrystallised twice from ethanol. The so purified compound (4.5 g.; 58% of theory; m.p. 209°-210° C. (decomp.)) contains, per mole of base, 1.5 mole of hydrogen chloride.

EXAMPLE 14

Analogously to the procedure in Example 1g, 4.5 g. of the 4-(1-cyanocyclopentyl)-1,2-diaminobenzene prepared in Example 13d are reacted with 5.7 g. anisic acid chloride to give 4.8 g. 5-(1-cyanocyclopentyl)-2-(4-methoxyphenyl)-benzimidazole as the hydrochloride (m.p. 250°-255° C. (decomp.)) which, for purification, is recrystallised from ethanol to give 3.9 g. (49% of theory) of colourless crystals; m.p. 253°-255° C. (decomp.).

EXAMPLE 15

5-(2-Cyanoprop-2-yl)-2-(4-pyridinyl)-benzimidazole (a) 90.2 g. 4-(2-Cyanoprop-2-yl)-1-nitrobenzene are hydrogenated in 1 liter methanol at 30° C. in the presence of 3 spoonfuls of Raney nickel until 33 liters of hydrogen have been taken up. After filtering and evaporating the filtrate in a vacuum, there are obtained 84.8 g. 4-(2-cyanoprop-2-yl)-aniline as a yellowish oil which is used without further purification.

(b) Analogously to the procedure in Example 13b, from 84.8 g. of the oil obtained in (a) there are obtained 84.3 g. 4-(2-cyanoprop-2-yl)-acetanilide as beige crystals; m.p. 105°–108° C.

(c) 53.1 g. 4-(2-Cyanoprop-2-yl)-acetanilide are nitrated in 160 ml. concentrated sulphuric acid with a mixture of 18.2 ml. 65% nitric acid (d=1.4) and 29.5 ml. concentrated sulphuric acid to give 38 g. 4-(2-cyanoprop-2-yl)-2-nitroacetanilide (58% of theory) which after recrystallisation from ethyl acetate, is obtained as yellowish crystals; m.p. 110°–111° C. (d) 38.0 g. 4-(2-Cyanoprop-2-yl)-2-nitroacetanilide are boiled under reflux in 200 ml. methanol and 20 ml. concentrated hydrochloric acid for 1.5 hours. The solvent is removed in a vacuum and the residue is digested with water to give 29.4 g. (93% of theory) 4-(2-cyanoprop-2-yl)-2-nitroaniline as orange-yellow crystals; m.p. 97°–99° C.

(e) From 18.5 g. 4-(2-cyanoprop-2-yl)-2-nitroaniline there are obtained analogously to the procedure in Example 13d, 15.8 g. (100% of theory) 4-(2-cyanoprop-2-yl)-1,2-diaminobenzene as a brownish oil.

(f) Analogously to the procedure in Example 1g, 15.8 g. 4-(2-cyanoprop-2-yl)-1,2-diaminobenzene is reacted with 24 g. isonicotinic acid chloride hydrochloride to give 18.9 g. of the title compound which is recrystallised from ethyl acetate to give 7.4 g. (31% of theory) of pale pink coloured crystals; m.p. 254°–255° C.

EXAMPLE 16

Analogously to the procedure of Example 1g, 4.1 g. of the 4-(2-cyanoprop-2yl)-1,2-diaminobenzene prepared in Example 15e is reacted with 6.0 g. anisic acid chloride to give 3.9 g. 5-(2-cyanoprop-2-yl)-2-(4-methoxyphenyl)-benzimidazole as hydrochloride which is recrystallized from ethanol to give 3.2 g. (42% of theory) of pale bluish coloured crystals; m.p. 253°–255° C.

EXAMPLE 17

5-(2-Isobutylamidomethylprop-2-yl)-2-(4-pyridinyl)-benzimidazole 3.5 g. of the 5-(2-Aminomethylprop-2-yl)-2-(4-pyridinyl)-benzimidazole (prepared in Example 1) in 30 ml. dichloromethane are mixed with 3 ml. isobutyric acid anhydride. The reaction mixture thereby warms up and the compound goes into solution. After stirring for 2 hours, sodium bicarbonate is added thereto and further stirred until the product is obtained first in a greasy form and then in crystalline form. The crystals are filtered off with suction and washed with water to give 4.3 g. of colourless crystals (m.p. 208°–211° C.) which are dissolved in 150 ml. water-saturated ethyl acetate and concentrated to about 100 ml., 3.4 g. (82% of theory) of the title compound thereby being obtained; m.p. 213°–214° C.

EXAMPLE 18

Analogously to Example 17, by reaction with acetic anhydride, there is obtained an 85% yield of 5-(2-acetamidomethylprop-2-yl)-2-(4-pyridinyl)-benzimidazole as colourless crystals which, after recrystallisation from ethyl acetate, have a melting point of 219°–225° C.

EXAMPLE 19

5-(2-Methylsulphonylaminomethyl-prop-2-yl)-2-(4-pyridinyl)-benzimidazole

To 2.0 g. of the 5-(2-aminomethylprop-2-yl)-2-(4-pyridinyl)-benzimidazole (prepared in Example 1) and 830 mg. triethylamine in 50 ml. dry dichloromethane are added dropwise, while cooling with ice water, 953 mg. mesyl chloride. The reaction mixture is stirred for 10 minutes and then 20 ml. water are added thereto. After filtering off with suction, washing with water and dichloromethane and recrystallising from water/ethanol (2:1 v/v), there are obtained 2.0 g. (85% of theory) of the title compound as a hydrate in the form of yellowish crystals which sinter above 130° C., again crystalline above 150° C. and then melt at 215°–216° C.

EXAMPLE 20

5-(2-Formylaminomethylprop-2-yl)-2-(4-piperidinyl)-benzimidazole 3.0 g. of the 5-(2-formylaminomethyl)prop-2-yl)-2-(4-pyridinyl)-benzimidazole prepared in Example 2 are hydrogenated in 50 ml. methanol in the presence of 1 ml. glacial acetic acid and 1 g. 10% palladium on charcoal for 6 hours at 50° C. and 5 bar hydrogen pressure. The reaction mixture is filtered, the filtrate is evaporated in a vacuum, the residue is digested with ethyl acetate, filtered off with suction and the residue is dissolved in 40 ml. hot dimethylformamide and filtered. After cooling, the filtrate is mixed with the same amount of ethyl acetate. After crystallisation, the product is filtered off with suction and washed with ethyl acetate to give 1.8 g. (59% of theory) of the title compound as colourless crystals; m.p. 234°–237° C.

EXAMPLE 21

5-(2-Formylaminomethylprop-2-yl)-2-(2-methoxy-5-methylsulphonylphenyl)-benzimidazole To 4.7 g. of the 5-(2-formylaminomethylprop-2-yl)-2-(2-methoxy-5-methylthiophenyl)-benzimidazole (prepared in Example 10b) in 130 ml. 80% formic acid are added 10 ml. hydrogen peroxide and heated for 2 hours to 50° C. For the removal of the peroxides, active charcoal is added thereto, stirred for 1 hour at 50° C., filtered off with suction and washed with water and dichloromethane to give 3.4 g. of crude product which is recrystallised from 200 ml. nitromethane with fullers' earth treatment to give 2.7 g. (53% of theory) of the title compound as colourless crystals; m.p. 235°–236° C.

EXAMPLE 22

5-(2-Formylaminomethylprop-2-yl)-2-(6-methoxypyridin-3-yl)-benzimidazole

To a solution of 3.5 g. of the 5-(2-formylaminomethylprop-2-yl)-2-(6-hydroxypyridin-3-yl)-benzimidazole (prepared in Example 4d) in 20 ml. water and 13.6 ml. 1N potassium hydroxide solution in ethanol is added 0.85 ml. methyl iodide, while cooling with water. After 24 hours, it is filtered off with suction and purified by column chromatography (silica gel, elution agent dichloromethane:methanolic ammonia=20:1 v/v). Appropriate fractions are combined, the solvent is removed in a vacuum and the residue is digested with ethanol/water. After filtering off with suction, there are obtained 2.2 g. (57% of theory) of the title compound which, per mole, still contains 0.75 mole of water, as colourless crystals which, in the air, become reddish coloured; m.p. 217°–221° C.

EXAMPLE 23

Analogously to Example 22, 4.8 g. 5-(2-formylaminomethylprop-2-yl)-2-(2-hydroxy-6-methylpyridin-3-yl)benzimidazole (prepared in Example 4a) are reacted with 1.5 ml. methyl iodide and, after column chromatographic purification, there are obtained 2.9 g. 5-(2-formylaminomethylprop-2-yl)-2-(2-methoxy-6-methylpyridin-3-yl)benzimidazole which is dissolved in hot dioxan, ethyl acetate is added thereto up to the commencement of turbidity and, after crystallisation, the crystals are filtered off with suction to give 2.2 g. (48% of theory) of the pure substance in the form of yellowish crystals; m.p. 201°–203° C.

EXAMPLE 24

5-(2-Aminocarbonylpropan-2-yl)-2-(4-pyridinyl)benzimidazole 3.7 g. of the 5-(2-cyanopropan-2-yl)-2-(4-pyridinyl)-benzimidazole (prepared in Example 15) are stirred for 3 hours at 50° C. in 40 ml. 80% sulphuric acid, the compound thereby slowly going into solution. The reaction mixture is then poured on to ice, rendered alkaline with ammonia, filtered off with suction and recrystallised from ethanol. There are obtained 2.4 g. (61% of theory) of the title compound in the form of colourless crystals; m.p. 274°–276° C.

EXAMPLE 25

5-[2-(Dimethylaminocarbonylaminomethyl)-propan-2-yl]-2-(4-pyridinyl)-benzimidazole To 0.25 g. 5-(2-aminoethylpropan-2-yl)-2-(4-pyridinyl)-benzimidazole (prepared in Example 1) in 6 ml. dichloromethane is added, with ice cooling, 0.13 ml. triethylamine and 0.1 g. N,N-dimethylcarbamic acid chloride. The reaction mixture is stirred for 20 hours at ambient temperature, the solvent is then removed in a vacuum, the residue is digested with water and the product is filtered off with suction and purified by filtration over a short column of silica gel (elution agent dichloromethane containing 5% methanol). The eluate is evaporated to dryness and the residue is crystallised from ethyl acetate. There is obtained 0.15 g. of the title compound; m.p. 136°–138° C.

EXAMPLE 26

5-(2-Acetamidomethyl-propan-2-yl)-2-(4-methylphenyl)benzimidazole

To 4.4 g. of the 4-(2-acetamidomethylpropan-2-yl)-1,2-diaminobenzene (prepared in Example 1f) in 120 ml. dry dichloromethane are added 3.3 ml. triethylamine and then, with ice cooling, 3.06 g. 4-methylbenzoic acid chloride. After stirring the reaction mixture for 3 hours at ambient temperature, the solvent is removed in a vacuum. The residue is dissolved in water and extracted three times with dichloromethane, the organic phase is dried over anhydrous sodium sulphate, filtered and the solvent is removed in a vacuum. The residue (6.7 g.) is dissolved in glacial acetic acid and stirred for 3 hours at 70° C. The solvent is removed in a vacuum and the residue is purified by column chromatography (silica gel; dichloromethane containing 5% methanol). There is obtained 1.55 g. of the title compound; m.p. 230°–232° C.

EXAMPLE 27

5-(2-Aminomethylpropan-2-yl)-2-(4-methylphenyl)benzimidazole 1.45 g. of the compound prepared in Example 26 is boiled under reflux for 48 hours in 35 ml. ethanol and 35 ml. concentrated hydrochloric acid. The solvent is removed in a vacuum and the residue is dissolved in water and neutralised with 2N aqueous ammonia solution. The substance which precipitates out is filtered off with suction. There is obtained 1.1 g. of the title compound; m.p. 45°–48° C.

EXAMPLE 28

5-(2-Formylaminomethylpropan-2-yl)-2-(4-methylphenyl)benzimidazole

The amine obtained in Example 27 is formylated analogously to Example 2 to give the title compound in a yield of 82% of theory; m.p. 193°–195° C., after recrystallisation from ethyl acetate.

EXAMPLE 29

5-(2-Acetamidomethylpropan-2-yl)-2-methylbenzimidazole 5.0 g. of the N,N'-diacetyl-4-(2-aminomethylpropan-2-yl)-2-nitroaniline (prepared in Example 1e) in 250 ml. ethanol are hydrogenated in the presence of 0.5 g. 10% palladium on charcoal at ambient temperature and normal pressure. After 1.25 liters of hydrogen have been taken up, the reaction mixture is filtered and the solvent is removed from the filtrate in a vacuum. The residue is stirred in 250 ml. glacial acetic acid for 3 hours at 70° C., the solvent then removed in a vacuum and the residue mixed with ethyl acetate and left to crystallise. There are obtained 2.4 g. of the title compound; m.p. 198°–201° C.

EXAMPLE 30

5-(2-Aminomethylpropan-2-yl)-2-methylbenzimidazole 2.4 g. 5-(2-acetamidomethylpropan-2-yl)-2-methylbenzimidazole (prepared in Example 29) are boiled under reflux for 24 hours in 60 ml. ethanol and 60 ml. concentrated hydrochloric acid. The solvent is then removed in a vacuum, the residue is neutralised with 2N aqueous ammonia solution and the organic phase is dried over anhydrous sodium sulphate. After filtration and evaporation, there is obtained 0.87 g. of the title compound in the form of an oil.

EXAMPLE 31

5-(2-Formylaminomethylpropan-2-yl)-2-methylbenzimidazole

In a manner analogous to Example 2, from 0.87 g. of the amine prepared in Example 30 there is obtained 0.5 g. of the title compound: m.p. 57°–60° C., after purification by column chromatography (silica gel; dichloromethane containing 2.5% methanol) and stirring with ligroin.

EXAMPLE 32

5-[2-(Isopropylcarbonylaminomethyl)-propan-2-yl]-2-(4-methoxyphenyl)-benzimidazole 1.9 g. 4-(2-Aminomethylpropan-2-yl)-2-(4-methoxyphenyl)-benzimidazole (obtained in Example 6) in 200 ml. dichloromethane are reacted with 2.5 ml. triethylamine and 0.82 g. isobutyric acid chloride at ambient temperature. After 10 hours, the solvent is removed in a vacuum and the residue is digested with water and 2N aqueous ammonia solution. The reaction mixture is extracted 4 times with dichloromethane and the organic phase is dried over anhydrous sodium sulphate, filtered and evaporated. Ethyl acetate is added thereto, a part thereof is distilled off with the dichloromethane and left to crystallise and the product is filtered with suction. The product is recrystallised from ethyl acetate to give 0.6 g. of the title compound; m.p. 218°–220° C.

EXAMPLE 33

5-(2-Methylsulphonylaminomethylpropan-2-yl)-2-(4-methoxyphenyl)-benzimidazole

The base is liberated from the hydrochloride obtained in Example 6 by stirring the compound with dichloromethane and a concentrated aqueous solution of ammonia until it has gone completely into solution, whereafter the dichloromethane phase is evaporated. To 4.1 g. of the 5-(2-aminomethylpropan-2-yl)-2-(4-methoxyphenyl)-benzimidazole thus obtained and 2.5 ml. Hünig base in 100 ml. dichloromethane is added dropwise, with stirring and cooling with ice water, 1.1 ml. mesyl chloride. The reaction mixture is stirred for 30 minutes at ambient temperature, mixed with water and the organic phase separated off and evaporated. The residue (5.1 g.) is dissolved in a little ethyl acetate, triturated, diluted with diethyl ether to 80 ml., filtered with suction and the product obtained recrystallised from ethyl acetate/diethyl ether to give 4.0 g. of the title compound in the form of colourless crystals; m.p. 146°–148° C.

EXAMPLE 34

5-(2-Methylsulphonylaminomethylpropan-2-yl)-2-(2-methoxy-4-methylmercaptophenyl)-benzimidazole Air is passed into a solution of 13 g. of 4-(2-acetamidomethylprop-2-yl)-1,2-diaminobenzene (obtained in Example 1f) and 18 g. of the bisulphite adduct of 2-methoxy-4-methylmercaptobenzaldehyde in 500 ml. methanol for 8 hours at ambient temperature. The reaction mixture is then evaporated and the residue purified by column chromatography (1.5 liters silica gel; trichloromethane:methanol:glacial acetic acid 10:1:0.2 v/v/v). There are obtained 16 g. 5-(2-acetamidomethylpropan-2-yl)-2-yl)-2-(2-methoxy-4-methylmercaptophenyl)-benzimidazole in the form of a brownish viscous mass which is boiled under reflux in 400 ml. ethanol and 100 ml. concentrated hydrochloric acid for 3 days. The reaction mixture is then evaporated and the residue is rendered alkaline with 2N aqueous sodium hydroxide solution and extracted with dichloromethane. The product is purified by column chromatography (silica gel; dichloromethane/methanolic ammonia 10:1 v/v) to give 5.4 g. 5-(2-aminomethylpropan-2-yl)-2-(2-methoxy-4-methylmercaptophenyl)-benzimidazole in the form of a brownish viscous mass, as well as 1 g. of unreacted starting material. 2.7 g. of the product are mesylated analogously to Example 33 to give 3.1 g. of the title compound in the form of a dihydrate; m.p 237°–239° C.

EXAMPLE 35

5-(2-Methylsulphonylaminomethylpropan-2-yl)-2-(2-methoxy-4-methylsulphinylphenyl)-benzimidazole 1.4 g. of the product of Example 34 in 28 ml. glacial acetic acid is oxidised with 0.4 ml. 30% hydrogen peroxide at ambient temperature. Over the course of 28 hours, the compound slowly goes into solution. The reaction mixture is diluted with water, buffered with a concentrated aqueous solution of ammonia and extracted with dichloromethane. The product is purified by column chromatography (800 ml. silica gel; dichloromethane/methanolic ammonia 20:1 v/v). The pure fractions are evaporated and the residue is digested with ethyl acetate to give 1.2 g. of the title compound; m.p. 126°–128° C.

EXAMPLE 36

5-(2-n-Propylsulphonylaminomethylpropan-2-yl)-2-(4-pyridinyl)-benzimidazole

Analogously to Example 33, from 5.3 g, 5-(2-aminomethylpropan-2-yl)-2-(4-pyridinyl)-benzimidazole and 2.8 ml. isopropanesulphonic acid chloride there is obtained the title compound in a yield of 42% of theory; m.p. 113°–120° C., after crystallisation from isopropanol. The compound contains 1 mole of isopropanol per mole.

EXAMPLE 37

5-(2-Isopropanesulphonylaminomethylpropan-2-yl)-(4-pyridinyl)-benzimidazole

Analogously to Example 33, from 5.3 g. 5-(2-aminomethylpropan-2-yl)-2-(4-pyridinyl)-benzimidazole and 2.8 ml. isopropanesulphonic acid chloride, there is obtained the title compound in a yield of 5% of theory; m.p. 126°–129° C., after crystallisation from isopropanol. The compound contains 1 mole of isopropanol per mole.

EXAMPLE 38

5-(2-Phenylsulphonylaminomethylpropan-2-yl)(4-pyridinyl)-benzimidazole

Analogously to Example 33, from 5.3 g. 5-(2-aminomethylpropan-2-yl)-2-(4-pyridinyl)-benzimidazole and 3.2 ml. phenylsulphonic acid chloride there is obtained the title compound in a yield of 50% of theory; m.p. 135°–140° C. after crystallisation from isopropanol. The compound contains 1 mole of isopropanol per mole.

EXAMPLE 39

5-(2-Acetamidomethylpropan-2-yl)-2-(4-imidazolyl)-benzimidazole 4.40 g. of the diamine prepared in Example 1f and 2.44 g. imidazole-4-carboxylic acid are heated under an atmosphere of nitrogen in 50 ml. polyphosphoric acid for 4.5 hours at 160° C. A further 2.44 g. imidazole-4-carboxylic acid are added thereto and heating at 160° C. is continued for 6 hours. After cooling, the reaction mixture is worked up with ice/water and then adjusted to pH 9 with a concentrated aqueous solution of ammonia. The supernatant liquid is decanted off, the greasy material remaining behind is digested with water, the residue is taken up in methanol/dichloromethane (1:3 v/v), dried over anhydrous sodium sulphate and distilled to dryness. The residue (3,95 g.) is dissolved in ethanol, acidified with ethanolic hydrochloric acid and evaporated. There is obtained 1.4 g. of the title compound in the form of a hydrochloride; m.p. 235°–237° C.

EXAMPLE 40

5-(2-Formylaminomethylpropan-2-yl)-2-(4-imidazolyl)-benzimidazole 1.2 g. of the compound obtained in Example 39 is boiled under reflux in 24 ml. ethanol and 28 ml. concentrated hydrochloric acid and worked up analogously to Example 2 to give 0.1 g. of the title compound in the form of the hydrochloride; m.p. 240°–246° C., after crystallisation from ethanolic hydrochloric acid.

EXAMPLE 41

5-(2-Aminomethylpropan-2-yl)-2-phenylbenzimidazole 4.4 g. of the diamine prepared in Example 1f and 2 ml. benzaldehyde in 50 ml. ethanol and 5 ml. glacial acetic acid are stirred at ambient temperature for 18 hours. The solvent is removed in a vacuum, rendered alkaline with 2N aqueous ammonia solution and extracted with dichloromethane. The organic phase is dried over anhydrous sodium sulphate and the solvent removed in a vacuum. The residue is boiled under reflux in 100 ml. ethanol and 20 ml. concentrated hydrochloric acid for 4 days. The solvent is then removed in a vacuum and the residue is adjusted to pH 9 with 2N aqueous ammonia solution to give 3 g. of the title compound; m.p. 185°–187° C.

EXAMPLE 42

5-(2-Aminomethylpropan-2-yl)-2-(4-hydroxyphenyl)-benzimidazole (m.p. 178°–182° C.) is obtained analogously to Example 41 by reaction with 4-hydroxybenzaldehyde.

EXAMPLE 43

5-(2-Aminomethylpropan-2-yl)-2-(2-furyl)-benzimidazole is obtained in the form of a foam analogously to Example 41 by reaction with furfural.

EXAMPLE 44

5-(2-Aminomethylpropan-2-yl)-2-(2-thienyl)-benzimidazole is obtained in the form of a foam analogously to Example 41 by reaction with thiophene-2-aldehyde.

EXAMPLE 45

Analogously to Example 2 are obtained:
(a) 5-(2-formylaminomethyl-propan-2-yl)-2-(2-ethoxycarbonylethyl)benzimidazole: amorph
(b) 5-(2-formylaminomethyl-propan-2-yl)-2-(4-dimethylaminophenyl)benzimidazole m.p. 130° C.
(c) 5-(2-formylaminomethyl-propan-2-yl)-2-cyclohexylbenzimidazole: amorph

EXAMPLE 46

Analogously to Example 18 are obtained:
(a) 5-(2-acetylaminomethyl-propan-2-yl)-2-hexylbenzimidazole: amorph
(b) 5-(2-acetylaminomethyl-propan-2-yl)-2-(4-methoxypheynl)benzimidazole 279°–282° C.

TEST REPORT

Method

The preparation of the heart muscle fibres and the experiments with chemically skinned heart muscle fibers were performed according the method described by Herzig et al. (1981a and 1981b).

Heart muscle preparations from pig hearts

Fiber bundles from the trabecula septomarginalis of the pig heart right ventricle were dissected into thin bundles of about 1 to 1.5 mm diameter and of about 15 mm length. They were extracted with a solution containing 50% glycerol, 1% Triton X 100, 5 mM ATP, 5 mM $MgCl_2$, 20 mM imidazole, 10 mM $NaN_3$, 4 mM EGTA, 2 mM dithioerythreitol (DTE) at a pH of 7.0 and at 4°–6° C. for 22 to 24 hours, whereby chemically skinned heart muscle fibers in a relaxed state were obtained. These chemically skinned preparations were preserved in the above mentioned solution without Triton X 100 at −18° C. until their use in the experiments.

Experiments with chemically skinned heart muscle fibers: isometric development of strength and examination of its modulation by Calcium and by test compounds Before use in the experiments the chemically skinned fibers were dissected into bundles of about 8–10 mm in length and of abaout 0.3 mm in diameter. The isometric development of force is measured by a transducer and a bridge amplifier together with a connected scanner.

Well defined concentrations of free calcium ions in the organ bath medium can be prepared by mixing appropriate volumes of a relaxing solution and activation solution. The final concentrations of the components of the relaxing solution (pH 6.7, 24° C.; 1 ml) are as follows: 35 mM Imidazole, 10 mM ATP, 12.5 mM $MgCl_2$, 5 mM sodium azide, 5 MM EGTA, 10 mM creatine phosphate and about 350 U creatine kinase. The activation solution additionally contains 5 mM calcium dichloride. By mixing appropriate volumes of activation solution and relaxing solution the concentration of free calcium ions in the organ bath varies between 0.4 uM and 45 uM (u=micro). The test compounds were added to the organ bath (1 ml) in a volume of 10 microliter.

The evaluation of a compound according to a possibly calcium sensitive effect on functionally isolated myofilaments was determined as follows: the isometric force development was measured with an increasing concentration of the test compound at a constant concentration of free calcium ions (1.6 uM), which initiates a submaximal pre-contraction. A compound is considered a calcium sensitizer when it effects an isometric increase in force at constant calcium concentrations.

TABLES

| Compound of Example | Increase in Force (%) | Highest Concentration Tested [uM] |
| --- | --- | --- |
| 7b | 119 | 500 |
| 12 | 177 | 500 |
| 13 | 106 | 100 |
| 15 | 142 | 500 |
| 24 | 148 | 500 |
| 33 | 244 | 500 |
| 36 | 135 | 500 |
| 37 | 310 | 500 |
| 40 | 113 | 500 |

It will be understood that the specification and examples are illustrative but not limitative of the present invention and that other embodiments within the spirit and scope of the invention will suggest themselves to those skilled in the art.

References

HERZIG, J. W.; FEILE, K.; RÜEGG, J. C.: Activating effects of AR-L 115 BS on the Ca++ sensitive force, stiffness and unloaded shortening velocity ($V_{max}$) in isolated contractile structures from mammalion heart muscle. Drug Res. 31, 188–191 (1981a)

HERZIG, J. W.; KÖHLER, G.; PFITZER, G.; RÜEGG, J. C.; WÖLFFLE, G.: Cyclic AMP inhibits contractility of detergent treated glycerol extracted cardiac muscle. Pflügers Arch. 391, 208–212 (1981b).

We claim:

1. A 5-alkylbenzimidazole of the formula:

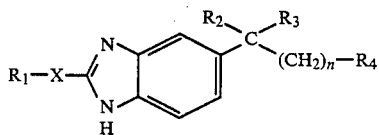

wherein

R₁ is a heterocyclic six-membered pyridyl or N-oxypyridyl ring optionally substituted by $C_1$–$C_6$ alkyl, $C_1$–$C_6$ alkoxy, $C_1$–$C_6$ alkylthio, hydroxyl, nitro, amino, halogen or cyano;

R₂ and R₃, which can be the same or different, are hydrogen or $C_1$–$C_6$ alkyl or R₂ and R₃, together with the carbon atom to which they are attached, represent a $C_3$–$C_7$ carbocyclic ring;

R₄ is cyano, aminocarbonyl, alkylaminocarbonyl, dialkylaminocarbonyl, hydrazinocarbonyl or amino wherein the hydrazinocarbonyl or the amino group may be substituted by a formyl, alkylcarbonyl, trifluoromethylcarbonyl, alkylsulphonyl, trifluoromethylsulphonyl, phenylsulphonyl, alkylaminocarbonyl or dialkylaminocarbonyl, wherein the alkyl moieties comprise up to 6 carbons;

X is a valency bond, $C_1$–$C_4$ alkylene, vinylene or imino group —NH— or carbonylamino group —CONH—; and n is 0 or 1 to 5;

or the tautomer thereof or a physiologically acceptable salt thereof with an inorganic and organic acid.

2. The compound of claim 1 wherein the heterocyclic ring substituents for R₁ are $C_1$–$C_4$ alkyl, $C_1$–$C_4$ alkoxy, $C_1$–$C_4$ alkylthio, or halogen.

3. The compound of claim 1 or 2 wherein the halogen is fluorine, chlorine or bromine.

4. The compound of claim 1 wherein R₂ or R₃ are methyl, ethyl, propyl or buytyl or R₂ and R₃ together form a cyclopentyl ring.

5. The compound of claim 1 wherein R₄ is cyano, aminocarbonyl, amino, formylamino, alkylcarbonylamino, trifluoromethylcarbonylamino, alkylsulphonylamino, trifluoromethylsulphonylamino, phenylsulphonylamino, alkylaminocarbonylamino or alkylcarbonylamino carbonylamino, whereby the alkyl moieties comprise up to 4 carbons.

6. The compound of claim 1 wherein X is methylene, ethylene, imino or carbonylamino.

7. The compound of claim 1 wherein R₁ is pyridyl or N-oxypyridyl;

R₂ and R₃ are methyl or together with the carbon to which they are attached form a cyclopentyl ring;

R₄ is cyano, aminocarbonyl, amino, formylamino, acetylamino, isopropylcarbonylamino, tert-butylcarbonylamino, dimethylaminocarbonylamino, methylsulphonylamino, n-propylsulphonylamino, isopropylsulphonylamino or phenylsulphonylamino;

X is a valency bond or a methylene group and n is 0 or 1.

8. A 5-alkyl-benzimidazole designated 5-(1-cyanocyclopentyl)-2-(4-pyridinyl)-benzimidazole.

9. A 5-alkyl-benzimidazole designated 5-(2-aminocarbonylpropan-2-yl)-2-(4-pyridinyl)-benzimidazole.

10. A 5-alkyl-benzimidazole designated of 5-(2-n-propylsulphonylamino-methylpropan-2-yl)-2-(4-pyridinyl)-benzimidazole.

11. A 5-alkyl-benzimidazole designated 5-(2-isopropanesulphonylamino-methylpropan-2-yl)-(4-pyridinyl)-benzimidazole.

12. A pharmaceutical composition containing an effective amount of one or more of the compound of claim 1, or 7 for the prophylaxis or treatment of heart and circulatory disease in a mammal in a pharmaceutically acceptable carrier wherein heart contractility is increased, blood pressure is lowered, microcirculation is improved or thrombocyte function is influenced.

13. A pharmaceutical composition for the treatment of heart and circulatory disease in a mammal wherein heart contractility is increased, blood pressure is lowered, microcirculation is improved or thrombocyte function is influenced comprising an effective amount of one or more of the compound from the group consisting of 5-(1-cyanocyclopentyl)-2-(4-pyridinyl)-benzimidazole, 5-(2-aminocarbonylpropan-2-yl)-2-(4-pyridinyl)-benzimidazole, 5-(2-n-propylsulphonylamino-methylpropan-2-yl)-2-(4-pyridinyl)-benzimidazole and 5-(2-isopropanesulphonylamino-methylpropan-2-yl)-(4-pyridinyl)-benzimidazole in a pharmaceutically acceptable carrier.

14. A method for the treatment or prophylaxis of heart and circulatory disease in a mammal wherein heart contractility is increased, blood pressure is lowered, microcirculation is improved or thrombocyte function is influenced comprising administering a pharmaceutically effective amount of one or more of the compound of claim 1 or 7.

15. A method for the treatment or prophylaxis of heart and circulatory disease in a mammal wherein heart contractility is increased, blood pressure is lowered, microcirculation is improved and thrombocyte function is influenced comprising administering a pharmaceutically effective amount of one or more of the compound designated 5-(1-cyanocyclopentyl)-2-(4-pyridinyl)-benzimidazole, 5-(2-aminocarbonylpropan-2-yl)-2-(4-pyridinyl)-benzimidazole, 5-(2-n-propylsulphonylamino-methylpropan-2-yl)-2-(4-pyridinyl)-benzimidazole and 5-(2-isopropanesulphonylamino-methylpropan-2-yl)-(4-pyridinyl)-benzimidazole.

16. The method of claim 14 wherein 10 to 500 mg per 75 kg body weight are administered per day.

17. The method of claim 15 wherein 10 to 500 mg per 75 kg body weight are administered per day.

* * * * *

UNITED STATES PATENT AND TRADEMARK OFFICE
CERTIFICATE OF CORRECTION

PATENT NO. : 4,882,342

DATED : November 21, 1989

INVENTOR(S) : Wolfgang Von Der Saal et al.

It is certified that error appears in the above-identified patent and that said Letters Patent is hereby corrected as shown below:

Column 3, line 52   Change "2,6-, 2,4- or 3,5-position" to -- 2,6-, 3,4- or 3,5-position --

Column 18, line 6   Change "6-methoxypyridin" to -- 6-methylpyridin --

Signed and Sealed this

Second Day of July, 1991

Attest:

Attesting Officer

HARRY F. MANBECK, JR.

Commissioner of Patents and Trademarks